US006329168B1

(12) United States Patent
Brown et al.

(10) Patent No.: US 6,329,168 B1
(45) Date of Patent: Dec. 11, 2001

(54) STREPTOCOCCUS PNEUMONIAE ISOLEUCYL TRNA SYNTHETASE

(75) Inventors: James R. Brown, Berwyn; Deborah D. Jaworski, Norristown, both of PA (US); Elizabeth J. Lawlor, Ruskington Sleaford (GB); Min Wang, Blue Bell, PA (US)

(73) Assignee: SmithKline Beecham Corp., Philadelphia, PA (US)

( * ) Notice: Subject to any disclaimer, the term of this patent is extended or adjusted under 35 U.S.C. 154(b) by 0 days.

(21) Appl. No.: 08/953,040

(22) Filed: Oct. 17, 1997

Related U.S. Application Data

(63) Continuation-in-part of application No. 08/844,084, filed on Apr. 18, 1997.

(30) Foreign Application Priority Data

Apr. 18, 1996 (GB) .................................................. 9608000

(51) Int. Cl.$^7$ ........................... C12P 21/06; C12N 15/00; C12N 1/20; C07H 21/04
(52) U.S. Cl. ....................... 435/69.1; 435/69.3; 435/70.1; 435/71.1; 435/193; 435/252.3; 435/254.11; 435/320.1; 435/325; 536/23.4; 536/23.7
(58) Field of Search .................................. 435/69.1, 69.3, 435/69.7, 70.1, 71.1, 71.2, 325, 252.3, 254.11, 320, 183, 193; 536/23.1, 23.2, 23.4, 23.7, 24.32; 935/9, 11, 12, 14, 22, 65, 66

(56) References Cited

FOREIGN PATENT DOCUMENTS

| | | |
|---|---|---|
| WO 94/28139 | 12/1994 | (WO) . |
| WO 95/09927 | 4/1995 | (WO) . |
| WO 97/39011 | 10/1997 | (WO) . |

OTHER PUBLICATIONS

Davis et al., "Microbiology", Harper and Rowe, Hagerston, p. 267, 1980.*
Lewin, B., "Genes IV", Oxford University Press, p. 810, 1990.*
Jobling et al., Mol. Microbiol., 5(7)1755–1767, 1991.*
Gerhold et al., BioEssays, 18(12):973–981, 1996.*
Wells et al., Journal of Leukocyte Biology, 61(5):545–550, 1997.*
Russell et al., Journal of Molecular Biology, 244:332–350, 1994.*
A.F. Chalker, et al., "Analysis and toxic overexpression in *Escherichia coli* of a *staphylococcal* gene encoding isoleucyl–tRNA synthetase", *Gene*, 141 pp. 103–108 (1994).
R. Calendar et al., "Purification and Physical Characterization of Tyrosyl Ribonucleic Acid Synthetases from *Escerichia coli* and *Bacillus subtilis*", *Biochemistry*, 5(5) p. 1681–1690 (1966).
J. Hughes et al., "How Does *Pseudomonas Fluorescens*, the Producing Organism of the Antibiotic Pseudomonic Acid A, Avoid Suicide?", *FEBS Letters*, 122(2) p. 322–324 (1980).
Chalker et al., "Analysis and Toxic Overexpression in *Escherichia coli* of a *Staphylococcal* Gene Encoding Isoleucyl–tRNA Synthetase," *Gene*, 141(1) p. 103–108 (1994).
Csank et al., "Isoleucyl–tRNA Synthetase from the Ciliated Protozoan *Tetrahymena thermophila*," *J. Biol. Chem.*, 267(7) p. 4592–4599 (1992).
Von Den Haar et al., "Target Directed Synthesis: The Aminoacyl–tRNA Synthetases as Possible Targets," *Angewandte Chemie*, 20(3) p. 217–302 (1981).
Meinnel et al., "Aminoacyl–tRNA Synthetases: Occurrence, Structure, and Function. IN: tRNA: Structure, Biosynthesis and Function," American Society of Microbiology, p. 251–292 (1995).
Linder et al, Journal of Bacteriology, 169(7): 3199–3208, 1967.*
Herzog et al, DNA and Cell Biology 12(6):465–471, 1993.*
Jazin et al, Regulatory Peptides, 47:247–258, 1993.*
Rudincer et al in "Peptide Harmones" Ed by Parsons J.A. University Park Press, Jun. 1976*
Burgess et al, The Journal of Cell Biology, 111:2129–2138, 1990.*
Lazar et al., Molecular and Cellular Biology, 8(3):1247–1252, 1988.*
Stratagic Product Calatog, 1991, p. 66.

* cited by examiner

*Primary Examiner*—Patricia A. Duffy
(74) *Attorney, Agent, or Firm*—Edward R. Gimmi; Thomas S. Deibert; William T. King

(57) ABSTRACT

The invention provides ileS polypeptides and DNA (RNA) encoding ileS polypeptides and methods for producing such polypeptides by recombinant techniques. Also provided are methods for utilizing ileS polypeptides to screen for antibacterial compounds.

12 Claims, No Drawings ary, in these and in other regards, the invention relates

SEQUENCE LISTING

```
<160> NUMBER OF SEQ ID NOS: 10

<210> SEQ ID NO 1
<211> LENGTH: 2793
<212> TYPE: DNA
<213> ORGANISM: Streptococcus pneumoniae

<400> SEQUENCE: 1
atgaaactca aagacaccct taatcttggg aaaactgaat tcccaatgcg tgcaggcctt      60
cctaccaaag agccagtttg gcaaaaggaa tgggaagatg caaaacttta tcaacgtcgt     120
caagaattga accaaggaaa acctcatttc accttgcatg atggccctcc atacgctaac     180
ggaaatatcc acgttggaca tgctatgaac aagatttcaa aagatatcat tgttcgttct     240
aagtctatgt caggatttta cgcgccattt attcctggtt gggatactca tggtctgcca     300
atcgagcaag tcttgtcaaa acaaggtgtc aaacgtaaag aaatggactt ggttgagtac     360
```

-continued

```
ttgaaacttt gccgtgagta cgctctttct caagtagata acaacgtga agattttaaa    420
cgtttgggtg tttctggtga ctgggaaaat ccatatgtga ccttgactcc tgactatgaa    480
gcagctcaaa ttcgtgtatt tggtgagatg gctaataagg gttatatcta ccgtggtgcc    540
aagccagttt actggtcatg gtcatctgag tcagcccttg ctgaagcaga gattgaatac    600
catgacttgg tttcaacttc cctttactat gccaacaagg taaaagatgg caaaggagtt    660
ctagatacag atacttatat cgttgtctgg acaacgactc catttaccat cacagcttct    720
cgtggtttga cggttggtgc agatattgat tacgttttgg ttcaacctgc tggtgaagct    780
cgtaagtttg tcgttgctgc tgaattattg actagcttgt ctgagaaatt tggctgggct    840
gatgttcaag ttttgaaaac ttaccgtggc aagaactta accacatcgt aacagaacac    900
ccatgggata cagctgtaga agagttggta attcttggtg accacgttac gactgactct    960
ggtacaggta ttgtccatac agcccctggt tttggtgagg acgactacaa tgttggtatt   1020
gctaataatc ttgaagtcgc agtgactgtt gatgaacgtg gtatcatgat gaagaatgct   1080
ggtcctgagt ttgaaggtca attctatgaa aaggtagttc caactgttat tgaaaaactt   1140
ggtaacctcc ttcttgccca agaagaaatc tctcactcat atccatttga ctggcgtact   1200
aagaaaccaa tcatctggcg tgcagttcca aatggtttg cctcagtttc taaattccgt    1260
caagaaatct tggacgaaat tgaaaagtg aaattccact cagaatgggg taaagtccgt    1320
ctttacaata tgatccgtga ccgtggtgac tgggttatct ctcgtcaacg tgcttggggt   1380
gttccacttc caatcttcta tgcagaagac ggtacagcta tcatggtagc tgaaacgatt   1440
gaacacgtag ctcaactttt tgaagaacat ggttcaagca tttggtggga acgtgatgcc   1500
aaagatctct tgccagaagg atttactcat ccaggttcac caaacggcga gttcaaaaaa   1560
gaaactgata tcatggacgt ttggtttgac tcaggttcat catggaatgg agtggtggta   1620
aaccgtcctg aattgactta cccagccgac ctttacctag aaggttctga ccaataccgt   1680
ggttggttta actcatcact tatcacatct gttgccaacc atggcgtagc accttacaaa   1740
caaatcttgt cacaaggttt tgcccttgat ggtaaaggtg agaagatgtc taaatctctt   1800
ggaaatacca ttgctccaag cgatgttgaa aaacaattcg gtgctgaaat cttgcgtctc   1860
tgggtaacaa gtgttgactc aagcaatgac gtgcgtatct ctatggatat tttgagccaa   1920
gtttctgaaa cttaccgtaa gattcgtaac actcttcgtt tcttgattgc caatacatct   1980
gactttaacc cagctcaaga tacagtcgct tacgatgagc ttcgttcagt tgataagtac   2040
atgacgattc gctttaacca gcttgtcaag accattcgtg atgcctatgc agactttgaa   2100
ttcttgacga tctacaaggc cttggtgaac tttatcaacg ttgacttgtc agccttctac   2160
cttgattttg ccaaagatgt tgtttacatt gaaggtgcca atcactgga acgccgtcaa    2220
atgcagactg tcttctatga cattcttgtc aaaatcacca aactcttgac accaatcctt   2280
cctcacactg cggaagaaat tggtcatat cttgagtttg aaacagaaga cttcgtccaa    2340
ttgtcagaat taccgaggc tcaaacttttt gctaatcaag aagaaatctt ggatacatgg   2400
gcagccttca tggacttccg tggacaagct caaaaagcct ggaagaagc tcgtaatgca    2460
aaagtaatcg gtaaatcact tgaagcacac ttgacagttt atccaaacga agttgtgaaa   2520
actctactcg aagcagtaaa cagcaatgtg gctcaacttt tgatcgtgtc agacttgacc   2580
atcgcagaag gaccagctcc agaagctgcc cttagcttcg aagatgtagc cttcacagtt   2640
gaacgcgctg caggtgaagt atgtgaccgt tgccgtcgta ttgacccaac aacagcagaa   2700
cgtagctacc aggcagttat ctgtgaccac tgtgcaagca tcgtagaaga aaactttgcg   2760
```
gaagcagtcg cagaaggatt tgaagagaaa taa 2793

<210> SEQ ID NO 2
<211> LENGTH: 930
<212> TYPE: PRT
<213> ORGANISM: Streptococcus pneumoniae

<400> SEQUENCE: 2

| | | | | | | | | | | | | | | |
|---|---|---|---|---|---|---|---|---|---|---|---|---|---|---|
| Met | Lys | Leu | Lys | Asp | Thr | Leu | Asn | Leu | Gly | Lys | Thr | Glu | Phe | Pro | Met |
| 1 | | | | 5 | | | | | 10 | | | | | 15 | |
| Arg | Ala | Gly | Leu | Pro | Thr | Lys | Glu | Pro | Val | Trp | Gln | Lys | Glu | Trp | Glu |
| | | | 20 | | | | | 25 | | | | | 30 | | |
| Asp | Ala | Lys | Leu | Tyr | Gln | Arg | Arg | Gln | Glu | Leu | Asn | Gln | Gly | Lys | Pro |
| | | 35 | | | | | 40 | | | | | 45 | | | |
| His | Phe | Thr | Leu | His | Asp | Gly | Pro | Pro | Tyr | Ala | Asn | Gly | Asn | Ile | His |
| | 50 | | | | | 55 | | | | | 60 | | | | |
| Val | Gly | His | Ala | Met | Asn | Lys | Ile | Ser | Lys | Asp | Ile | Ile | Val | Arg | Ser |
| 65 | | | | | 70 | | | | | 75 | | | | | 80 |
| Lys | Ser | Met | Ser | Gly | Phe | Tyr | Ala | Pro | Phe | Ile | Pro | Gly | Trp | Asp | Thr |
| | | | | 85 | | | | | 90 | | | | | 95 | |
| His | Gly | Leu | Pro | Ile | Glu | Gln | Val | Leu | Ser | Lys | Gln | Gly | Val | Lys | Arg |
| | | | 100 | | | | | 105 | | | | | 110 | | |
| Lys | Glu | Met | Asp | Leu | Val | Glu | Tyr | Leu | Lys | Leu | Cys | Arg | Glu | Tyr | Ala |
| | | 115 | | | | | 120 | | | | | 125 | | | |
| Leu | Ser | Gln | Val | Asp | Lys | Gln | Arg | Glu | Asp | Phe | Lys | Arg | Leu | Gly | Val |
| | 130 | | | | | 135 | | | | | 140 | | | | |
| Ser | Gly | Asp | Trp | Glu | Asn | Pro | Tyr | Val | Thr | Leu | Thr | Pro | Asp | Tyr | Glu |
| 145 | | | | | 150 | | | | | 155 | | | | | 160 |
| Ala | Ala | Gln | Ile | Arg | Val | Phe | Gly | Glu | Met | Ala | Asn | Lys | Gly | Tyr | Ile |
| | | | | 165 | | | | | 170 | | | | | 175 | |
| Tyr | Arg | Gly | Ala | Lys | Pro | Val | Tyr | Trp | Ser | Trp | Ser | Ser | Glu | Ser | Ala |
| | | | 180 | | | | | 185 | | | | | 190 | | |
| Leu | Ala | Glu | Ala | Glu | Ile | Glu | Tyr | His | Asp | Leu | Val | Ser | Thr | Ser | Leu |
| | | 195 | | | | | 200 | | | | | 205 | | | |
| Tyr | Tyr | Ala | Asn | Lys | Val | Lys | Asp | Gly | Lys | Gly | Val | Leu | Asp | Thr | Asp |
| | 210 | | | | | 215 | | | | | 220 | | | | |
| Thr | Tyr | Ile | Val | Val | Trp | Thr | Thr | Pro | Phe | Thr | Ile | Thr | Ala | Ser |
| 225 | | | | | 230 | | | | | 235 | | | | | 240 |
| Arg | Gly | Leu | Thr | Val | Gly | Ala | Asp | Ile | Asp | Tyr | Val | Leu | Val | Gln | Pro |
| | | | 245 | | | | | 250 | | | | | 255 | | |
| Ala | Gly | Glu | Ala | Arg | Lys | Phe | Val | Val | Ala | Ala | Glu | Leu | Leu | Thr | Ser |
| | | 260 | | | | | 265 | | | | | 270 | | | |
| Leu | Ser | Glu | Lys | Phe | Gly | Trp | Ala | Asp | Val | Gln | Val | Leu | Glu | Thr | Tyr |
| | 275 | | | | | 280 | | | | | 285 | | | | |
| Arg | Gly | Gln | Glu | Leu | Asn | His | Ile | Val | Thr | Glu | His | Pro | Trp | Asp | Thr |
| 290 | | | | | 295 | | | | | 300 | | | | | |
| Ala | Val | Glu | Glu | Leu | Val | Ile | Leu | Gly | Asp | His | Val | Thr | Thr | Asp | Ser |
| 305 | | | | | 310 | | | | | 315 | | | | | 320 |
| Gly | Thr | Gly | Ile | Val | His | Thr | Ala | Pro | Gly | Phe | Gly | Glu | Asp | Asp | Tyr |
| | | | | 325 | | | | | 330 | | | | | 335 | |
| Asn | Val | Gly | Ile | Ala | Asn | Asn | Leu | Glu | Val | Ala | Val | Thr | Val | Asp | Glu |
| | | | 340 | | | | | 345 | | | | | 350 | | |
| Arg | Gly | Ile | Met | Met | Lys | Asn | Ala | Gly | Pro | Glu | Phe | Glu | Gly | Gln | Phe |
| | | 355 | | | | | 360 | | | | | 365 | | | |

```
Tyr Glu Lys Val Val Pro Thr Val Ile Glu Lys Leu Gly Asn Leu Leu
    370                 375                 380

Leu Ala Gln Glu Glu Ile Ser His Ser Tyr Pro Phe Asp Trp Arg Thr
385                 390                 395                 400

Lys Lys Pro Ile Ile Trp Arg Ala Val Pro Gln Trp Phe Ala Ser Val
                405                 410                 415

Ser Lys Phe Arg Gln Glu Ile Leu Asp Glu Ile Glu Lys Val Lys Phe
                420                 425                 430

His Ser Glu Trp Gly Lys Val Arg Leu Tyr Asn Met Ile Arg Asp Arg
            435                 440                 445

Gly Asp Trp Val Ile Ser Arg Gln Arg Ala Trp Gly Val Pro Leu Pro
    450                 455                 460

Ile Phe Tyr Ala Glu Asp Gly Thr Ala Ile Met Val Ala Glu Thr Ile
465                 470                 475                 480

Glu His Val Ala Gln Leu Phe Glu His Gly Ser Ser Ile Trp Trp
                485                 490                 495

Glu Arg Asp Ala Lys Asp Leu Leu Pro Glu Gly Phe Thr His Pro Gly
                500                 505                 510

Ser Pro Asn Gly Glu Phe Lys Lys Glu Thr Asp Ile Met Asp Val Trp
            515                 520                 525

Phe Asp Ser Gly Ser Ser Trp Asn Gly Val Val Asn Arg Pro Glu
    530                 535                 540

Leu Thr Tyr Pro Ala Asp Leu Tyr Leu Glu Gly Ser Asp Gln Tyr Arg
545                 550                 555                 560

Gly Trp Phe Asn Ser Ser Leu Ile Thr Ser Val Ala Asn His Gly Val
                565                 570                 575

Ala Pro Tyr Lys Gln Ile Leu Ser Gln Gly Phe Ala Leu Asp Gly Lys
            580                 585                 590

Gly Glu Lys Met Ser Lys Ser Leu Gly Asn Thr Ile Ala Pro Ser Asp
            595                 600                 605

Val Glu Lys Gln Phe Gly Ala Glu Ile Leu Arg Leu Trp Val Thr Ser
    610                 615                 620

Val Asp Ser Ser Asn Asp Val Arg Ile Ser Met Asp Ile Leu Ser Gln
625                 630                 635                 640

Val Ser Glu Thr Tyr Arg Lys Ile Arg Asn Thr Leu Arg Phe Leu Ile
                645                 650                 655

Ala Asn Thr Ser Asp Phe Asn Pro Ala Gln Asp Thr Val Ala Tyr Asp
            660                 665                 670

Glu Leu Arg Ser Val Asp Lys Tyr Met Thr Ile Arg Phe Asn Gln Leu
            675                 680                 685

Val Lys Thr Ile Arg Asp Ala Tyr Ala Asp Phe Glu Phe Leu Thr Ile
    690                 695                 700

Tyr Lys Ala Leu Val Asn Phe Ile Asn Val Asp Leu Ser Ala Phe Tyr
705                 710                 715                 720

Leu Asp Phe Ala Lys Asp Val Val Tyr Ile Glu Gly Ala Lys Ser Leu
                725                 730                 735

Glu Arg Arg Gln Met Gln Thr Val Phe Tyr Asp Ile Leu Val Lys Ile
            740                 745                 750

Thr Lys Leu Leu Thr Pro Ile Leu Pro His Thr Ala Glu Glu Ile Trp
    755                 760                 765

Ser Tyr Leu Glu Phe Glu Thr Glu Asp Phe Val Gln Leu Ser Glu Leu
    770                 775                 780
```

```
Pro Glu Ala Gln Thr Phe Ala Asn Gln Glu Glu Ile Leu Asp Thr Trp
785                 790                 795                 800

Ala Ala Phe Met Asp Phe Arg Gly Gln Ala Gln Lys Ala Leu Glu Glu
            805                 810                 815

Ala Arg Asn Ala Lys Val Ile Gly Lys Ser Leu Glu Ala His Leu Thr
        820                 825                 830

Val Tyr Pro Asn Glu Val Val Lys Thr Leu Leu Glu Ala Val Asn Ser
    835                 840                 845

Asn Val Ala Gln Leu Leu Ile Val Ser Asp Leu Thr Ile Ala Glu Gly
850                 855                 860

Pro Ala Pro Glu Ala Ala Leu Ser Phe Glu Asp Val Ala Phe Thr Val
865                 870                 875                 880

Glu Arg Ala Ala Gly Glu Val Cys Asp Arg Cys Arg Arg Ile Asp Pro
                885                 890                 895

Thr Thr Ala Glu Arg Ser Tyr Gln Ala Val Ile Cys Asp His Cys Ala
            900                 905                 910

Ser Ile Val Glu Glu Asn Phe Ala Glu Ala Val Ala Glu Gly Phe Glu
        915                 920                 925

Glu Lys
    930

<210> SEQ ID NO 3
<211> LENGTH: 24
<212> TYPE: DNA
<213> ORGANISM: Streptococcus pneumoniae

<400> SEQUENCE: 3
atgaaactca aagacaccct taat                                          24

<210> SEQ ID NO 4
<211> LENGTH: 24
<212> TYPE: DNA
<213> ORGANISM: Streptococcus pneumoniae

<400> SEQUENCE: 4
ttatttctct tcaaatcctt ctgc                                          24

<210> SEQ ID NO 5
<211> LENGTH: 815
<212> TYPE: DNA
<213> ORGANISM: Streptococcus pneumoniae

<400> SEQUENCE: 5
atgaaactca aagacaccct taatcttggg aaaactgaat tcccaatgcg tgcaggcctt    60
cctaccaaag agccagtttg caaaaggaa  tgggaagatg caaaacttta tcaacgtcgt   120
caagaattga accaaggaaa acctcatttc accttgcatg atggccctcc atacgctaac   180
ggaaatatcc acgttggaca tgctatgaac aagatttcaa agatatcat tgttcgttct   240 aagtctatgt caggatttta cgcgccattt attcctggtt gggatactca tggtctgcca   300
atcgagcaag tcttgtcaaa acaaggtgtc aaacgtaaag aaatggactt ggttgagtac   360
ttgaaacttt gccgtgagta cgctctttct caagtagata acaacgtga agatttaa     420 cgtttgggtg tttctggtga ctgggaaaat ccatatgtga ccttgactcc tgactatgaa   480
gcagctcaaa tcgtgtatt tggtgagatg gctaataagg ttatatcta ccgtggtgcc    540 aagccagttt actggtcatg gtcatctgag tcagcccttg ctgaagcaga gattgaatac   600
catgacttgg tttcaacttc cctttactat gccaacaagg taaagatgg caaaggagtt    660
```

-continued

```
ctagatacag atacttatat cgttgtctgg acaacgactc catttaccat cacagcttct      720
cgtggtttga cggttggtgc agatattgat tacgttttgg ttcaacctgc tggtgaagct      780
cgtaagtttg tcgttgctgc tgaattattg actag                                 815
```

<210> SEQ ID NO 6
<211> LENGTH: 271
<212> TYPE: PRT
<213> ORGANISM: Streptococcus pneumoniae

<400> SEQUENCE: 6

```
Met Lys Leu Lys Asp Thr Leu Asn Leu Gly Lys Thr Glu Phe Pro Met
 1               5                  10                  15
Arg Ala Gly Leu Pro Thr Lys Glu Pro Val Trp Gln Lys Glu Trp Glu
            20                  25                  30
Asp Ala Lys Leu Tyr Gln Arg Arg Gln Glu Leu Asn Gln Gly Lys Pro
        35                  40                  45
His Phe Thr Leu His Asp Gly Pro Tyr Ala Asn Gly Asn Ile His
    50                  55                  60
Val Gly His Ala Met Asn Lys Ile Ser Lys Asp Ile Ile Val Arg Ser
65                  70                  75                  80
Lys Ser Met Ser Gly Phe Tyr Ala Pro Phe Ile Pro Gly Trp Asp Thr
                85                  90                  95
His Gly Leu Pro Ile Glu Gln Val Leu Ser Lys Gln Gly Val Lys Arg
            100                 105                 110
Lys Glu Met Asp Leu Val Glu Tyr Leu Lys Leu Cys Arg Glu Tyr Ala
        115                 120                 125
Leu Ser Gln Val Asp Lys Gln Arg Glu Asp Phe Lys Arg Leu Gly Val
    130                 135                 140
Ser Gly Asp Trp Glu Asn Pro Tyr Val Thr Leu Thr Pro Asp Tyr Glu
145                 150                 155                 160
Ala Ala Gln Ile Arg Val Phe Gly Glu Met Ala Asn Lys Gly Tyr Ile
                165                 170                 175
Tyr Arg Gly Ala Lys Pro Val Tyr Trp Ser Trp Ser Ser Glu Ser Ala
            180                 185                 190
Leu Ala Glu Ala Glu Ile Glu Tyr His Asp Leu Val Ser Thr Ser Leu
        195                 200                 205
Tyr Tyr Ala Asn Lys Val Lys Asp Gly Lys Gly Val Leu Asp Thr Asp
    210                 215                 220
Thr Tyr Ile Val Val Trp Thr Thr Pro Phe Thr Ile Thr Ala Ser
225                 230                 235                 240
Arg Gly Leu Thr Val Gly Ala Asp Ile Asp Tyr Val Leu Val Gln Pro
                245                 250                 255
Ala Gly Glu Ala Arg Lys Phe Val Val Ala Ala Glu Leu Leu Thr
            260                 265                 270
```

<210> SEQ ID NO 7
<211> LENGTH: 25
<212> TYPE: DNA
<213> ORGANISM: Streptococcus pneumoniae

<400> SEQUENCE: 7

```
ttatttctct tcaaatcctt ctgcg                                            25
```

<210> SEQ ID NO 8
<211> LENGTH: 1977
<212> TYPE: DNA

<213> ORGANISM: Streptococcus pneumoniae

<400> SEQUENCE: 8

| | | | | | |
|---|---|---|---|---|---|
| ttgtctgaga | aatttggctg | ggctgatgtt | caagttttgg | aaacttaccg | tggccaagaa | 60 |
| cttaaccaca | tcgtaacaga | acacccatgg | gatacagctg | tagaagagtt | ggtaattctt | 120 |
| ggtgaccacg | ttacgactga | ctctggtaca | ggtattgtcc | atacagcccc | tggttttggt | 180 |
| gaggacgact | acaatgttgg | tattgctaat | aatcttgaag | tcgcagtgac | tgttgatgaa | 240 |
| cgtggtatca | tgatgaagaa | tgctggtcct | gagtttgaag | gtcaattcta | tgaaaaggta | 300 |
| gttccaactg | ttattgaaaa | acttggtaac | ctccttcttg | cccaagaaga | aatctctcac | 360 |
| tcatatccat | ttgactggcg | tactaagaaa | ccaatcatct | ggcgtgcagt | tccacaatgg | 420 |
| tttgcctcag | tttctaaatt | ccgtcaagaa | atcttggacg | aaattgaaaa | agtgaaattc | 480 |
| cactcagaat | gggtaaagt | ccgtctttac | aatatgatcc | gtgaccgtgg | tgactgggtt | 540 |
| atctctcgtc | aacgtgcttg | gggtgttcca | cttccaatct | tctatgcaga | agacggtaca | 600 |
| gctatcatgg | tagctgaaac | gattgaacac | gtagctcaac | tttttgaaga | acatggttca | 660 |
| agcatttggt | gggaacgtga | tgccaaagat | ctcttgccag | aaggatttac | tcatccaggt | 720 |
| tcaccaaacg | gcgagttcaa | aaagaaaact | gatatcatgg | acgtttggtt | tgactcaggt | 780 |
| tcatcatgga | atggagtggt | ggtaaaccgt | cctgaattga | cttacccagc | cgaccttta | 840 |
| ctagaaggtt | ctgaccaata | ccgtggttgg | tttaactcat | cacttatcac | atctgttgcc | 900 |
| aaccatggcg | tagcacctta | caaacaaatc | ttgtcacaag | gttttgccct | tgatggtaaa | 960 |
| ggtgagaaga | tgtctaaatc | tcttggaaat | accattgctc | caagcgatgt | tgaaaaacaa | 1020 |
| ttcggtgctg | aaatcttgcg | tctctgggta | caagtgttg | actcaagcaa | tgacgtgcgt | 1080 |
| atctctatgg | atattttgag | ccaagtttct | gaaacttacc | gtaagattcg | taacactctt | 1140 |
| cgtttcttga | ttgccaatac | atctgacttt | aacccagctc | aagatacagt | cgcttacgat | 1200 |
| gagcttcgtt | cagttgataa | gtacatgacg | attcgcttta | accagcttgt | caagaccatt | 1260 |
| cgtgatgcct | atgcagactt | tgaattcttg | acgatctaca | aggccttggt | gaactttatc | 1320 |
| aacgttgact | tgtcagcctt | ctaccttgat | tttgccaaag | atgttgttta | cattgaaggt | 1380 |
| gccaaatcac | tggaacgccg | tcaaatgcag | actgtcttct | atgacattct | tgtcaaaatc | 1440 |
| accaaactct | tgacaccaat | ccttcctcac | actgcggaag | aaatttggtc | atatcttgag | 1500 |
| tttgaaacag | aagacttcgt | ccaattgtca | gaattaccag | aggctcaaac | ttttgctaat | 1560 |
| caagaagaaa | tcttggatac | atgggcagcc | ttcatggact | tccgtggaca | agctcaaaaa | 1620 |
| gccttggaag | aagctcgtaa | tgcaaaagta | atcggtaaat | cacttgaagc | acacttgaca | 1680 |
| gtttatccaa | acgaagttgt | gaaaactcta | ctcgaagcag | taaacagcaa | tgtggctcaa | 1740 |
| cttttgatcg | tgtcagactt | gaccatcgca | gaaggaccag | ctccagaagc | tgcccttagc | 1800 |
| ttcgaagatg | tagccttcac | agttgaacgc | gctgcaggtg | aagtatgtga | ccgttgccgt | 1860 |
| cgtattgacc | caacaacagc | agaacgtagc | taccaggcag | ttatctgtga | ccactgtgca | 1920 |
| agcatcgtag | aagaaaactt | tgcggaagca | gtcgcagaag | gatttgaaga | gaaataa | 1977 |

<210> SEQ ID NO 9
<211> LENGTH: 658
<212> TYPE: PRT
<213> ORGANISM: Streptococcus pneumoniae

<400> SEQUENCE: 9

Leu Ser Glu Lys Phe Gly Trp Ala Asp Val Gln Val Leu Glu Thr Tyr

-continued

```
  1                   5                   10                  15
Arg Gly Gln Glu Leu Asn His Ile Val Thr Glu His Pro Trp Asp Thr
                 20                  25                  30

Ala Val Glu Glu Leu Val Ile Leu Gly Asp His Val Thr Thr Asp Ser
                 35                  40                  45

Gly Thr Gly Ile Val His Thr Ala Pro Gly Phe Gly Glu Asp Asp Tyr
             50                  55                  60

Asn Val Gly Ile Ala Asn Asn Leu Glu Val Ala Val Thr Val Asp Glu
65                   70                  75                  80

Arg Gly Ile Met Met Lys Asn Ala Gly Pro Glu Phe Glu Gly Gln Phe
                     85                  90                  95

Tyr Glu Lys Val Val Pro Thr Val Ile Glu Lys Leu Gly Asn Leu Leu
                100                 105                 110

Leu Ala Gln Glu Glu Ile Ser His Ser Tyr Pro Phe Asp Trp Arg Thr
                115                 120                 125

Lys Lys Pro Ile Ile Trp Arg Ala Val Pro Gln Trp Phe Ala Ser Val
                130                 135                 140

Ser Lys Phe Arg Gln Glu Ile Leu Asp Glu Ile Glu Lys Val Lys Phe
145                 150                 155                 160

His Ser Glu Trp Gly Lys Val Arg Leu Tyr Asn Met Ile Arg Asp Arg
                     165                 170                 175

Gly Asp Trp Val Ile Ser Arg Gln Arg Ala Trp Gly Val Pro Leu Pro
                180                 185                 190

Ile Phe Tyr Ala Glu Asp Gly Thr Ala Ile Met Val Ala Glu Thr Ile
                195                 200                 205

Glu His Val Ala Gln Leu Phe Glu Glu His Gly Ser Ser Ile Trp Trp
                210                 215                 220

Glu Arg Asp Ala Lys Asp Leu Leu Pro Glu Gly Phe Thr His Pro Gly
225                 230                 235                 240

Ser Pro Asn Gly Glu Phe Lys Lys Glu Thr Asp Ile Met Asp Val Trp
                245                 250                 255

Phe Asp Ser Gly Ser Ser Trp Asn Gly Val Val Asn Arg Pro Glu
                260                 265                 270

Leu Thr Tyr Pro Ala Asp Leu Tyr Leu Glu Gly Ser Asp Gln Tyr Arg
                275                 280                 285

Gly Trp Phe Asn Ser Ser Leu Ile Thr Ser Val Ala Asn His Gly Val
                290                 295                 300

Ala Pro Tyr Lys Gln Ile Leu Ser Gln Gly Phe Ala Leu Asp Gly Lys
305                 310                 315                 320

Gly Glu Lys Met Ser Lys Ser Leu Gly Asn Thr Ile Ala Pro Ser Asp
                325                 330                 335

Val Glu Lys Gln Phe Gly Ala Glu Ile Leu Arg Leu Trp Val Thr Ser
                340                 345                 350

Val Asp Ser Ser Asn Asp Val Arg Ile Ser Met Asp Ile Leu Ser Gln
                355                 360                 365

Val Ser Glu Thr Tyr Arg Lys Ile Arg Asn Thr Leu Arg Phe Leu Ile
                370                 375                 380

Ala Asn Thr Ser Asp Phe Asn Pro Ala Gln Asp Thr Val Ala Tyr Asp
385                 390                 395                 400

Glu Leu Arg Ser Val Asp Lys Tyr Met Thr Ile Arg Phe Asn Gln Leu
                405                 410                 415

Val Lys Thr Ile Arg Asp Ala Tyr Ala Asp Phe Glu Phe Leu Thr Ile
                420                 425                 430
```

-continued

```
Tyr Lys Ala Leu Val Asn Phe Ile Asn Val Asp Leu Ser Ala Phe Tyr
        435                 440                 445

Leu Asp Phe Ala Lys Asp Val Val Tyr Ile Glu Gly Ala Lys Ser Leu
    450                 455                 460

Glu Arg Arg Gln Met Gln Thr Val Phe Tyr Asp Ile Leu Val Lys Ile
465                 470                 475                 480

Thr Lys Leu Leu Thr Pro Ile Leu Pro His Thr Ala Glu Glu Ile Trp
                485                 490                 495

Ser Tyr Leu Glu Phe Glu Thr Glu Asp Phe Val Gln Leu Ser Glu Leu
            500                 505                 510

Pro Glu Ala Gln Thr Phe Ala Asn Gln Glu Glu Ile Leu Asp Thr Trp
        515                 520                 525

Ala Ala Phe Met Asp Phe Arg Gly Gln Ala Gln Lys Ala Leu Glu Glu
    530                 535                 540

Ala Arg Asn Ala Lys Val Ile Gly Lys Ser Leu Glu Ala His Leu Thr
545                 550                 555                 560

Val Tyr Pro Asn Glu Val Val Lys Thr Leu Leu Glu Ala Val Asn Ser
                565                 570                 575

Asn Val Ala Gln Leu Leu Ile Val Ser Asp Leu Thr Ile Ala Glu Gly
            580                 585                 590

Pro Ala Pro Glu Ala Ala Leu Ser Phe Glu Asp Val Ala Phe Thr Val
        595                 600                 605

Glu Arg Ala Ala Gly Glu Val Cys Asp Arg Cys Arg Arg Ile Asp Pro
    610                 615                 620

Thr Thr Ala Glu Arg Ser Tyr Gln Ala Val Ile Cys Asp His Cys Ala
625                 630                 635                 640

Ser Ile Val Glu Glu Asn Phe Ala Glu Ala Val Ala Glu Gly Phe Glu
                645                 650                 655

Glu Lys

<210> SEQ ID NO 10
<211> LENGTH: 390
<212> TYPE: DNA
<213> ORGANISM: Streptococcus pneumoniae

<400> SEQUENCE: 10
caactttttg aagaacatgg ttcaagcatt tggtgggaac gtgatgccaa agatctcttg      60
ccagaaggat ttactcatcc aggttcacca aacggcgagt tcaaaaaaga aactgatatc     120
atggacgttt ggtttgactc aggttcatca tggaatggag tggtggtaaa ccgtcctgaa     180
ttgacttacc cagccgacct ttacctagaa ggttctgacc aataccgtgg ttggtttaac     240
tcatcactta tcacatctgt tgccaaccat ggcgtagcac cttacaaaca aatcttgtca     300
caaggttttg cccttgatgg taaaggtgag aagatgtcta aatctcttgg aaataccatt     360
gctccaagcg atgttgaaaa acaattcggg                                      390
```

STREPTOCOCCUS PNEUMONIAE ISOLEUCYL TRNA SYNTHETASE

RELATED APPLICATIONS

This is a continuation-in part of U.S. patent application Ser. No. 08/844,084 filed Apr. 18, 1997, claiming benefit of GB Patent Application Number 9608000.7, filed Apr. 18, 1996.

FIELD OF THE INVENTION

This invention relates to newly identified polynucleotides and polypeptides, and their production and uses, as well as their variants, agonists and antagonists, and their uses. In particular, in these and in other regards, the invention relates to novel polynucleotides and polypeptides of the isoleucyl tRNA synthetase family, hereinafter referred to as "ileS".

BACKGROUND OF THE INVENTION

The Streptococci make up a medically important genera of microbes known to cause several types of disease in humans, including, for example, otitis media, conjunctivitis, pneumonia, bacteremia, meningitis, sinusitis, pleural empyema and endocarditis, and most particularly meningitis, such as for example infection of cerebrospinal fluid. Since its isolation more than 100 years ago, *Streptococcus pneumoniae* has been one of the more intensively studied microbes. For example, much of our early understanding that DNA is, in fact, the genetic material was predicated on the work of Griffith and of Avery, Macleod and McCarty using this microbe. Despite the vast amount of research with *S. pneumoniae*, many questions concerning the virulence of this microbe remain. It is particularly preferred to employ Streptococcal genes and gene products as targets for the development of antibiotics.

The frequency of *Streptococcus pneumoniae* infections has risen dramatically in the past 20 years. This has been attributed to the emergence of multiply antibiotic resistant strains and an increasing population of people with weakened immune systems. It is no longer uncommon to isolate *Streptococcus pneumoniae* strains which are resistant to some or all of the standard antibiotics. This has created a demand for both new anti-microbial agents and diagnostic tests for this organism.

t-RNA synthetases have a primary role in protein synthesis according to the following scheme:

Enzyme+ATP+AA⇌Enzyme.AA-AMP+PPi

Enzyme.AA-AMP+t-RNA⇌Enzyme+AMP+AA-t-RNA

in which AA is an amino acid.

Inhibition of this process leads to a reduction in the levels of charged t-RNA and this triggers a cascade of responses known as the stringent response, the result of which is the induction of a state of dormancy in the organism. As such selective inhibitors of bacterial t-RNA synthetase have potential as antibacterial agents. One example of such is mupirocin which is a selective inhibitor of isoleucyl t-RNA synthetase. Other t-RNA synthetases are now being examined as possible anti-bacterial targets, this process being greatly assisted by the isolation of the synthetase.

Clearly, there is a need for factors, such as the novel compounds of the invention, that have a present benefit of being useful to screen compounds for antibiotic activity. Such factors are also useful to determine their role in pathogenesis of infection, dysfunction and disease. There is also a need for identification and characterization of such factors and their antagonists and agonists which can play a role in preventing, ameliorating or correcting infections, dysfunctions or diseases.

The polypeptides of the invention have amino acid sequence homology to a known *Staphylococcus aureus* isoleucyl tRNA synthetase protein.

SUMMARY OF THE INVENTION

It is an object of the invention to provide polypeptides that have been identified as novel ileS polypeptides by homology between the amino acid sequence set out in Table 1 [SEQ ID NO: 2, 6 and 9] and a known amino acid sequence or sequences of other proteins such as *Staphylococcus aureus* isoleucyl tRNA synthetase protein.

It is a further object of the invention to provide polynucleotides that encode ileS polypeptides, particularly polynucleotides that encode the polypeptide herein designated ileS.

In a particularly preferred embodiment of the invention the polynucleotide comprises a region encoding ileS polypeptides comprising the sequence set out in Table 1 [SEQ ID NO: 1, 5, 8 and 10] which includes, for example, a full length gene, or a variant thereof.

In another particularly preferred embodiment of the invention there is a novel ileS protein from Streptococcus pneumoniae comprising the amino acid sequence of Table 1 [SEQ ID NO: 2, 6 and 9], or a variant thereof.

In accordance with another aspect of the invention there is provided an isolated nucleic acid molecule encoding a mature polypeptide expressible by the *Streptococcus pneumoniae* 0100993 strain contained in the deposited strain.

A further aspect of the invention there are provided isolated nucleic acid molecules encoding ileS, particularly *Streptococcus pneumoniae* ileS, including mRNAs, cDNAs, genomic DNAs. Further embodiments of the invention include biologically, diagnostically, prophylactically, clinically or therapeutically useful variants thereof, and compositions comprising the same.

In accordance with another aspect of the invention, there is provided the use of a polynucleotide of the invention for therapeutic or prophylactic purposes, in particular genetic immunization. Among the particularly preferred embodiments of the invention are naturally occurring allelic variants of ileS and polypeptides encoded thereby.

Another aspect of the invention there are provided novel polypeptides of *Streptococcus pneumoniae* referred to herein as ileS as well as biologically, diagnostically, prophylactically, clinically or therapeutically useful variants thereof, and compositions comprising the same.

Among the particularly preferred embodiments of the invention are variants of ileS polypeptide encoded by naturally occurring alleles of the ileS gene.

In a preferred embodiment of the invention there are provided methods for producing the aforementioned ileS polypeptides.

In accordance with yet another aspect of the invention, there are provided inhibitors to such polypeptides, useful as antibacterial agents, including, for example, antibodies.

In accordance with certain preferred embodiments of the invention, there are provided products, compositions and methods for assessing ileS expression, treating disease, for example, otitis media, conjunctivitis, pneumonia, bacteremia, meningitis, sinusitis, pleural empyema and endocarditis, and most particularly meningitis, such as for example infection of cerebrospinal fluid, assaying genetic variation, and administering a ileS polypeptide or polynucleotide to an organism to raise an immunological response against a bacteria, especially a *Streptococcus pneumoniae* bacteria.

In accordance with certain preferred embodiments of this and other aspects of the invention there are provided polynucleotides that hybridize to ileS polynucleotide sequences, particularly under stringent conditions.

In certain preferred embodiments of the invention there are provided antibodies against ileS polypeptides.

In other embodiments of the invention there are provided methods for identifying compounds which bind to or otherwise interact with and inhibit or activate an activity of a polypeptide or polynucleotide of the invention comprising: contacting a polypeptide or polynucleotide of the invention with a compound to be screened under conditions to permit binding to or other interaction between the compound and the polypeptide or polynucleotide to assess the binding to or other interaction with the compound, such binding or interaction being associated with a second component capable of providing a detectable signal in response to the binding or interaction of the polypeptide or polynucleotide with the compound; and determining whether the compound binds to or otherwise interacts with and activates or inhibits an activity of the polypeptide or polynucleotide by detecting the presence or absence of a signal generated from the binding or interaction of the compound with the polypeptide or polynucleotide.

In accordance with yet another aspect of the invention, there are provided ileS agonists and antagonists, preferably bacteriostatic or bactericidal agonists and antagonists.

In a further aspect of the invention there are provided compositions comprising a ileS polynucleotide or a ileS polypeptide for administration to a cell or to a multicellular organism.

Various changes and modifications within the spirit and scope of the disclosed invention will become readily apparent to those skilled in the art from reading the following descriptions and from reading the other parts of the present disclosure.

GLOSSARY

The following definitions are provided to facilitate understanding of certain terms used frequently herein.

"Host cell" is a cell which has been transformed or transfected, or is capable of transformation or transfection by an exogenous polynucleotide sequence.

"Identity," as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part I, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991; and Carillo, H., and Lipman, D., SIAM *J. Applied Math.*, 48: 1073 (1988). Preferred methods to determine identity are designed to give the largest match between the sequences tested. Methods to determine identity and similarity are codified in publicly available computer programs. Preferred computer program methods to determine identity and similarity between two sequences include, but are not limited to, the GCG program package (Devereux, J., et al., *Nucleic Acids Research* 12(1): 387 (1984)), BLASTP, BLASTN, and FASTA (Atschul, S. F. et al., *J. Molec. Biol.* 215: 403–410 (1990). The BLAST X program is publicly available from NCBI and other sources (*BLAST Manual*, Altschul, S., et al., NCBI NLM NIH Bethesda, Md. 20894; Altschul, S., et al., *J. Mol. Biol.* 215: 403–410 (1990). As an illustration, by a polynucleotide having a nucleotide sequence having at least, for example, 95% "identity" to a reference nucleotide sequence of SEQ ID NO: 1 it is intended that the nucleotide sequence of the polynucleotide is identical to the reference sequence except that the polynucleotide sequence may include up to five point mutations per each 100 nucleotides of the reference nucleotide sequence of SEQ ID NO: 1. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. Analogously, by a polypeptide having an amino acid sequence having at least, for example, 95% identity to a reference amino acid sequence of SEQ ID NO: 2 is intended that the amino acid sequence of the polypeptide is identical to the reference sequence except that the polypeptide sequence may include up to five amino acid alterations per each 100 amino acids of the reference amino acid of SEQ ID NO: 2. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

"Isolated" means altered "by the hand of man" from its natural state, ie., if it occurs in nature, it has been changed or removed from its original environment, or both. For example, a polynucleotide or a polypeptide naturally present in a living organism is not "isolated," but the same polynucleotide or polypeptide separated from the coexisting materials of its natural state is "isolated", as the term is employed herein.

"Polynucleotide(s)" generally refers to any polyribonucleotide or polydeoxribonucleotide, which may be unmodified RNA or DNA or modified RNA or DNA. "Polynucleotide(s)" include, without limitation, single- and double-stranded DNA, DNA that is a mixture of single- and double-stranded regions or single-, double- and triple-stranded regions, single- and double-stranded RNA, and RNA that is mixture of single- and double-stranded regions, hybrid molecules comprising DNA and RNA that may be single-stranded or, more typically, double-stranded, or triple-stranded regions, or a mixture of single- and double-stranded regions. In addition, "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. As used herein, the term "polynucleotide(s)" also includes DNAs or RNAs as described above that contain one or more modified bases. Thus, DNAs or RNAs with backbones modified for stability or for other reasons are "polynucleotide(s)" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term "polynucleotide(s)" as it is employed herein embraces such chemically, enzymatically or metabolically modified forms of polynucleotides, as well as the chemical forms of DNA and RNA characteristic of viruses and cells, including, for example, simple and complex cells. "Polynucleotide(s)" also embraces short polynucleotides often referred to as oligonucleotide(s).

"Polypeptide(s)" refers to any peptide or protein comprising two or more amino acids joined to each other by peptide bonds or modified peptide bonds. "Polypeptide(s)" refers to both short chains, commonly referred to as peptides, oligopeptides and oligomers and to longer chains generally referred to as proteins. Polypeptides may contain amino acids other than the 20 gene encoded amino acids. "Polypeptide(s)" include those modified either by natural processes, such as processing and other post-translational modifications, but also by chemical modification techniques. Such modifications are well described in basic texts and in more detailed monographs, as well as in a voluminous research literature, and they are well known to those of skill in the art. It will be appreciated that the same type of modification may be present in the same or varying degree at several sites in a given polypeptide. Also, a given polypeptide may contain many types of modifications. Modifications can occur anywhere in a polypeptide, including the peptide backbone, the amino acid side-chains, and the amino or carboxyl termini. Modifications include, for example, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, glycosylation, lipid attachment, sulfation, gamma-carboxylation of glutamic acid residues, hydroxylation and ADP-ribosylation, selenoylation, sulfation, transfer-RNA mediated addition of amino acids to proteins, such as arginylation, and ubiquitination. See, for instance, *PROTEINS—STRUCTURE AND MOLECULAR PROPERTIES*, 2nd Ed., T. E. Creighton, W. H. Freeman and Company, New York (1993) and Wold, F., Posttranslational Protein Modifications: Perspectives and Prospects, pgs. 1–12 in *POSTTRANSLATIONAL COVALENT MODIFICATION OF PROTEINS*, B. C. Johnson, Ed., Academic Press, New York (1983); Seifter et al., *Meth. Enzymol.* 182:626–646 (1990) and Rattan et al., *Protein Synthesis: Posttranslational Modifications and Aging*, Ann. N.Y. Acad. Sci. 663: 48–62 (1992). Polypeptides may be branched or cyclic, with or without branching. Cyclic, branched and branched circular polypeptides may result from post-translational natural processes and may be made by entirely synthetic methods, as well.

"Variant(s)" as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques, by direct synthesis, and by other recombinant methods known to skilled artisans.

DESCRIPTION OF THE INVENTION

The invention relates to novel ileS polypeptides and polynucleotides as described in greater detail below. In particular, the invention relates to polypeptides and polynucleotides of a novel ileS of *Streptococcus pneumoniae*, which is related by amino acid sequence homology to *Staphylococcus aureus* isoleucyl tRNA synthetase polypeptide. The invention relates especially to ileS having the nucleotide and amino acid sequences set out in Table 1 [SEQ ID NO: 1] and Table 1 [SEQ ID NO: 2] respectively, and to the ileS nucleotide sequences of the DNA in the deposited strain and amino acid sequences encoded thereby.

TABLE 1 ileS Polynucleotide and Polypeptide Sequences (A) Sequences from *Streptococcus pneumoniae* ileS polynucleotide sequence [SEQ ID NO:1].

```
   5'-1 ATGAAACTCA AAGACACCCT TAATCTTGGG AAAACTGAAT TCCCAATGCG

51 TGCAGGCCTT CCTACCAAAG AGCCAGTTTG GCAAAAGGAA TGGGAAGATG

101 CAAAACTTTA TCAACGTCGT CAAGAATTGA ACCAAGGAAA ACCTCATTTC

151 ACCTTGCATG ATGGCCCTCC ATACGCTAAC GGAAATATCC ACGTTGGACA
```

TABLE 1-continued ileS Polynucleotide and Polypeptide Sequences

```
 201 TGCTATGAAC AAGATTTCAA AAGATATCAT TGTTCGTTCT AAGTCTATGT
 251 CAGGATTTTA CGCGCCATTT ATTCCTGGTT GGGATACTCA TGGTCTGCCA
 301 ATCGAGCAAG TCTTGTCAAA ACAAGGTGTC AAACGTAAAG AAATGGACTT
 351 GGTTGAGTAC TTGAAACTTT GCCGTGAGTA CGCTCTTTCT CAAGTAGATA
 401 AACAACGTGA AGATTTTAAA CGTTTGGGTG TTTCTGGTGA CTGGGAAAAT
 451 CCATATGTGA CCTTGACTCC TGACTATGAA GCAGCTCAAA TTCGTGTATT
 501 TGGTGAGATG GCTAATAAGG GTTATATCTA CCGTGGTGCC AAGCCAGTTT
 551 ACTGGTCATG GTCATCTGAG TCAGCCCTTG CTGAAGCAGA GATTGAATAC
 601 CATGACTTGG TTTCAACTTC CCTTTACTAT GCCAACAAGG TAAAAGATGG
 651 CAAAGGAGTT CTAGATACAG ATACTTATAT CGTTGTCTGG ACAACGACTC
 701 CATTTACCAT CACAGCTTCT CGTGGTTTGA CGGTTGGTGC AGATATTGAT
 751 TACGTTTTGG TTCAACCTGC TGGTGAAGCT CGTAAGTTTG TCGTTGCTGC
 801 TGAATTATTG ACTAGCTTGT CTGAGAAATT TGGCTGGGCT GATGTTCAAG
 851 TTTTGGAAAC TTACCGTGGC AAGAACTTA ACCACATCGT AACAGAACAC
 901 CCATGGGATA CAGCTGTAGA AGAGTTGGTA ATTCTTGGTG ACCACGTTAC
 951 GACTGACTCT GGTACAGGTA TTGTCCATAC AGCCCCTGGT TTTGGTGAGG
1001 ACGACTACAA TGTTGGTATT GCTAATAATC TTGAAGTCGC AGTGACTGTT
1051 GATGAACGTG GTATCATGAT GAAGAATGCT GGTCCTGAGT TTGAAGGTCA
1101 ATTCTATGAA AGGTAGTTC CAACTGTTAT TGAAAAACTT GGTAACCTCC
1151 TTCTTGCCCA AGAAGAAATC TCTCACTCAT ATCCATTTGA CTGGCGTACT
1201 AAGAAACCAA TCATCTGGCG TGCAGTTCCA CAATGGTTTG CCTCAGTTTC
1251 TAAATTCCGT CAAGAAATCT TGGACGAAAT TGAAAAAGTG AAATTCCACT
1301 CAGAATGGGG TAAAGTCCGT CTTTACAATA TGATCCGTGA CCGTGGTGAC
1351 TGGGTTATCT CTCGTCAACG TGCTTGGGGT GTTCCACTTC CAATCTTCTA
1401 TGCAGAAGAC GGTACAGCTA TCATGGTAGC TGAAACGATT GAACACGTAG
1451 CTCAACTTTT TGAAGAACAT GGTTCAAGCA TTTGGTGGGA ACGTGATGCC
1501 AAAGATCTCT TGCCAGAAGG ATTTACTCAT CCAGGTTCAC AAACGGCGA
1551 GTTCAAAAAA GAAACTGATA TCATGGACGT TTGGTTTGAC TCAGGTTCAT
1601 CATGGAATGG AGTGGTGGTA AACCGTCCTG AATTGACTTA CCCAGCCGAC
1651 CTTTACCTAG AAGGTTCTGA CCAATACCGT GGTTGGTTTA ACTCATCACT
1701 TATCACATCT GTTGCCAACC ATGGCGTAGC ACCTTACAAA CAAATCTTGT
1751 CACAAGGTTT TGCCCTTGAT GGTAAAGGTG AGAAGATGTC TAAATCTCTT
1801 GGAAATACCA TTGCTCCAAG CGATGTTGAA AAACAATTCG GTGCTGAAAT
1851 CTTGCGTCTC TGGGTAACAA GTGTTGACTC AAGCAATGAC GTGCGTATCT
1901 CTATGGATAT TTTGAGCCAA GTTTCTGAAA CTTACCGTAA GATTCGTAAC
1951 ACTCTTCGTT TCTTGATTGC CAATACATCT GACTTTAACC CAGCTCAAGA
2001 TACAGTCGCT TACGATGAGC TTCGTTCAGT TGATAAGTAC ATGACGATTC
2051 GCTTTAACCA GCTTGTCAAG ACCATTCGTG ATGCCTATGC AGACTTTGAA
```

TABLE 1-continued ileS Polynucleotide and Polypeptide Sequences

```
2101 TTCTTGACGA TCTACAAGGC CTTGGTGAAC TTTATCAACG TTGACTTGTC

2151 AGCCTTCTAC CTTGATTTTG CCAAAGATGT TGTTTACATT GAAGGTGCCA

2201 AATCACTGGA ACGCCGTCAA ATGCAGACTG TCTTCTATGA CATTCTTGTC

2251 AAAATCACCA AACTCTTGAC ACCAATCCTT CCTCACACTG CGGAAGAAAT

2301 TTGGTCATAT CTTGAGTTTG AAACAGAAGA CTTCGTCCAA TTGTCAGAAT

2351 TACCAGAGGC TCAAACTTTT GCTAATCAAG AAGAAATCTT GGATACATGG

2401 GCAGCCTTCA TGGACTTCCG TGGACAAGCT CAAAAAGCCT TGGAAGAAGC

2451 TCGTAATGCA AAAGTAATCG GTAAATCACT TGAAGCACAC TTGACAGTTT

2501 ATCCAAACGA AGTTGTGAAA ACTCTACTCG AAGCAGTAAA CAGCAATGTG

2551 GCTCAACTTT TGATCGTGTC AGACTTGACC ATCGCAGAAG GACCAGCTCC

2601 AGAAGCTGCC CTTAGCTTCG AAGATGTAGC CTTCACAGTT GAACGCGCTG

2651 CAGGTGAAGT ATGTGACCGT TGCCGTCGTA TTGACCCAAC AACAGCAGAA

2701 CGTAGCTACC AGGCAGTTAT CTGTGACCAC TGTGCAAGCA TCGTAGAAGA

2751 AAACTTTGCG GAAGCAGTCG CAGAAGGATT TGAAGAGAAA TAA-3'
```

(B) ileS polypeptide sequence deduced from the polynucleotide sequence in this table [SEQ ID NO:2].

```
NH₂-1 MKLKDTLNLG KTEFPMRAGL PTKEPVWQKE WEDAKLYQRR QELNQGKPHF

51 TLHDGPPYAN GNIHVGHAMN KISKDIIVRS KSMSGFYAPF IPGWDTHGLP

101 IEQVLSKQGV KRKEMDLVEY LKLCREYALS QVDKQREDFK RLGVSGDWEN

151 PYVTLTPDYE AAQIRVFGEM ANKGYIYRGA KPVYWSWSSE SALAEAEIEY

201 HDLVSTSLYY ANKVKDGKGV LDTDTYIVVW TTTPFTITAS RGLTVGADID

251 YVLVQPAGEA RKFVVAAELL TSLSEKFGWA DVQVLETYRG QELNHIVTEH

301 PWDTAVEELV ILGDHVTTDS GTGIVHTAPG FGEDDYNVGI ANNLEVAVTV

351 DERGIMMKNA GPEFEGQFYE KVVPTVIEKL GNLLLAQEEI SHSYPFDWRT

401 KKPIIWRAVP QWFASVSKFR QEILDEIEKV KFHSEWGKVR LYNMIRDRGD

451 WVISRQRAWG VPLPIFYAED GTAIMVAETI EHVAQLFEEH GSSIWWERDA

501 KDLLPEGFTH PGSPNGEFKK ETDIMDVWFD SGSSWNGVVV NRPELTYPAD

551 LYLEGSDQYR GWFNSSLITS VANHGVAPYK QILSQGFALD GKGEKMSKSL

601 GNTIAPSDVE KQFGAEILRL WVTSVDSSND VRISMDILSQ VSETYRKIRN

651 TLRFLIANTS DFNPAQDTVA YDELRSVDKY MTIRFNQLVK TIRDAYADFE

701 FLTIYKALVN FINVDLSAFY LDFAKDVVYI EGAKSLERRQ MQTVFYDILV

751 KITKLLTPIL PHTAEEIWSY LEFETEDFVQ LSELPEAQTF ANQEEILDTW

801 AAFMDFRGQA QKALEEARNA KVIGKSLEAH LTVYPNEVVK TLLEAVNSNV

851 AQLLIVSDLT IAEGPAPEAA LSFEDVAFTV ERAAGEVCDR CRRIDPTTAE

901 RSYQAVICDH CASIVEENFA EAVAEGFEEK-COOH
```

(C) Polynucleotide sequence embodiments [SEQ ID NO: 1].

```
X-(R₁)ₙ-1 ATGAAACTCA AAGACACCCT TAATCTTGGG AAAACTGAAT TCCCAATGCG

51 TGCAGGCCTT CCTACCAAAG AGCCAGTTTG GCAAAAGGAA TGGGAAGATG

101 CAAAACTTTA TCAACGTCGT CAAGAATTGA ACCAAGGAAA ACCTCATTTC

151 ACCTTGCATG ATGGCCCTCC ATACGCTAAC GGAAATATCC ACGTTGGACA
```

TABLE 1-continued ileS Polynucleotide and Polypeptide Sequences

```
 201 TGCTATGAAC AAGATTTCAA AAGATATCAT TGTTCGTTCT AAGTCTATGT
 251 CAGGATTTTA CGCGCCATTT ATTCCTGGTT GGGATACTCA TGGTCTGCCA
 301 ATCGAGCAAG TCTTGTCAAA ACAAGGTGTC AAACGTAAAG AAATGGACTT
 351 GGTTGAGTAC TTGAAACTTT GCCGTGAGTA CGCTCTTTCT CAAGTAGATA
 401 AACAACGTGA AGATTTTAAA CGTTTGGGTG TTTCTGGTGA CTGGGAAAAT
 451 CCATATGTGA CCTTGACTCC TGACTATGAA GCAGCTCAAA TTCGTGTATT
 501 TGGTGAGATG GCTAATAAGG GTTATATCTA CCGTGGTGCC AAGCCAGTTT
 551 ACTGGTCATG GTCATCTGAG TCAGCCCTTG CTGAAGCAGA GATTGAATAC
 601 CATGACTTGG TTTCAACTTC CCTTTACTAT GCCAACAAGG TAAAGATGG
 651 CAAAGGAGTT CTAGATACAG ATACTTATAT CGTTGTCTGG ACAACGACTC
 701 CATTTACCAT CACAGCTTCT CGTGGTTTGA CGGTTGGTGC AGATATTGAT
 751 TACGTTTTGG TTCAACCTGC TGGTGAAGCT CGTAAGTTTG TCGTTGCTGC
 801 TGAATTATTG ACTAGCTTGT CTGAGAAATT TGGCTGGGCT GATGTTCAAG
 851 TTTTGGAAAC TTACCGTGGC AAGAACTTA ACCACATCGT AACAGAACAC
 901 CCATGGGATA CAGCTGTAGA AGAGTTGGTA ATTCTTGGTG ACCACGTTAC
 951 GACTGACTCT GGTACAGGTA TTGTCCATAC AGCCCCTGGT TTTGGTGAGG
1001 ACGACTACAA TGTTGGTATT GCTAATAATC TTGAAGTCGC AGTGACTGTT
1051 GATGAACGTG GTATCATGAT GAAGAATGCT GGTCCTGAGT TTGAAGGTCA
1101 ATTCTATGAA AAGGTAGTTC CAACTGTTAT TGAAAAACTT GGTAACCTCC
1151 TTCTTGCCCA AGAAGAAATC TCTCACTCAT ATCCATTTGA CTGGCGTACT
1201 AAGAAACCAA TCATCTGGCG TGCAGTTCCA CAATGGTTTG CCTCAGTTTC
1251 TAAATTCCGT CAAGAAATCT TGGACGAAAT TGAAAAGTG AAATTCCACT
1301 CAGAATGGGG TAAAGTCCGT CTTTACAATA TGATCCGTGA CCGTGGTGAC
1351 TGGGTTATCT CTCGTCAACG TGCTTGGGGT GTTCCACTTC AATCTTCTA
1401 TGCAGAAGAC GGTACAGCTA TCATGGTAGC TGAAACGATT GAACACGTAG
1451 CTCAACTTTT TGAAGAACAT GGTTCAAGCA TTTGGTGGGA ACGTGATGCC
1501 AAAGATCTCT TGCCAGAAGG ATTTACTCAT CCAGGTTCAC AAACGGCGA
1551 GTTCAAAAAA GAAACTGATA TCATGGACGT TTGGTTTGAC TCAGGTTCAT
1601 CATGGAATGG AGTGGTGGTA AACCGTCCTG AATTGACTTA CCCAGCCGAC
1651 CTTTACCTAG AAGGTTCTGA CCAATACCGT GGTTGGTTTA ACTCATCACT
1701 TATCACATCT GTTGCCAACC ATGGCGTAGC ACCTTACAAA CAAATCTTGT
1751 CACAAGGTTT TGCCCTTGAT GGTAAAGGTG AGAAGATGTC TAAATCTCTT
1801 GGAAATACCA TTGCTCCAAG CGATGTTGAA AAACAATTCG GTGCTGAAAT
1851 CTTGCGTCTC TGGGTAACAA GTGTTGACTC AAGCAATGAC GTGCGTATCT
1901 CTATGGATAT TTTGAGCCAA GTTTCTGAAA CTTACCGTAA GATTCGTAAC
1951 ACTCTTCGTT TCTTGATTGC CAATACATCT GACTTTAACC CAGCTCAAGA
2001 TACAGTCGCT TACGATGAGC TTCGTTCAGT TGATAAGTAC ATGACGATTC
2051 GCTTTAACCA GCTTGTCAAG ACCATTCGTG ATGCCTATGC AGACTTTGAA
2101 TTCTTGACGA TCTACAAGGC CTTGGTGAAC TTTATCAACG TTGACTTGTC
```

TABLE 1-continued ileS Polynucleotide and Polypeptide Sequences

```
2151 AGCCTTCTAC CTTGATTTTG CCAAAGATGT TGTTTACATT GAAGGTGCCA

2201 AATCACTGGA ACGCCGTCAA ATGCAGACTG TCTTCTATGA CATTCTTGTC

2251 AAAATCACCA AACTCTTGAC ACCAATCCTT CCTCACACTG CGGAAGAAAT

2301 TTGGTCATAT CTTGAGTTTG AAACAGAAGA CTTCGTCCAA TTGTCAGAAT

2351 TACCAGAGGC TCAAACTTTT GCTAATCAAG AAGAAATCTT GGATACATGG

2401 GCAGCCTTCA TGGACTTCCG TGGACAAGCT CAAAAAGCCT TGGAAGAAGC

2451 TCGTAATGCA AAAGTAATCG GTAAATCACT TGAAGCACAC TTGACAGTTT

2501 ATCCAAACGA AGTTGTGAAA ACTCTACTCG AAGCAGTAAA CAGCAATGTG

2551 GCTCAACTTT TGATCGTGTC AGACTTGACC ATCGCAGAAG GACCAGCTCC

2601 AGAAGCTGCC CTTAGCTTCG AAGATGTAGC CTTCACAGTT GAACGCGCTG

2651 CAGGTGAAGT ATGTGACCGT TGCCGTCGTA TTGACCCAAC AACAGCAGAA

2701 CGTAGCTACC AGGCAGTTAT CTGTGACCAC TGTGCAAGCA TCGTAGAAGA

2751 AAACTTTGCG GAAGCAGTCG CAGAAGGATT TGAAGAGAAA TAA-(R₂)ₙ-Y
```

(D) Polypeptide sequence embodiments [SEQ ID NO:2].

```
X-(R₁)ₙ-1 MKLKDTLNLG KTEFPMRAGL PTKEPVWQKE WEDAKLYQRR QELNQGKPHF

51 TLHDGPPYAN GNIHVGHAMN KISKDIIVRS KSMSGFYAPF IPGWDTHGLP

101 IEQVLSKQGV KRKEMDLVEY LKLCREYALS QVDKQREDFK RLGVSGDWEN

151 PYVTLTPDYE AAQIRVFGEM ANKGYIYRGA KPVYWSWSSE SALAEAEIEY

201 HDLVSTSLYY ANKVKDGKGV LDTDTYIVVW TTTPFTITAS RGLTVGADID

251 YVLVQPAGEA RKFVVAAELL TSLSEKFGWA DVQVLETYRG QELNHIVTEH

301 PWDTAVEELV ILGDHVTTDS GTGIVHTAPG FGEDDYNVGI ANNLEVAVTV

351 DERGIMMKNA GPEFEGQFYE KVVPTVIEKL GNLLLAQEEI SHSYPFDWRT

401 KKPIIWRAVP QWFASVSKFR QEILDEIEKV KFHSEWGKVR LYNMIRDRGD

451 WVISRQRAWG VPLPIFYAED GTAIMVAETI EHVAQLFEEH GSSIWWERDA

501 KDLLPEGFTH PGSPNGEFKK ETDIMDVWFD SGSSWNGVVV NRPELTYPAD

551 LYLEGSDQYR GWFNSSLITS VANHGVAPYK QILSQGFALD GKGEKMSKSL

601 GNTIAPSDVE KQFGAEILRL WVTSVDSSND VRISMDILSQ VSETYRKIRN

651 TLRFLIANTS DFNPAQDTVA YDELRSVDKY MTIRFNQLVK TIRDAYADFE

701 FLTIYKALVN FINVDLSAFY LDFAKDVVYI EGAKSLERRQ MQTVFYDILV

751 KITKLLTPIL PHTAEEIWSY LEFETEDFVQ LSELPEAQTF ANQEEILDTW

801 AAFMDFRGQA QKALEEARNA KVIGKSLEAH LTVYPNEVVK TLLEAVNSNV

851 AQLLIVSDLT IAEGPAPEAA LSFEDVAFTV ERAAGEVCDR CRRIDPTTAE

901 RSYQAVICDH CASIVEENFA EAVAEGFEEK-(R₂)ₙ-Y
```

(E) Sequences from *Streptococcus pneumoniae* ileS polynucleotide sequence.

Fragment 1 [SEQ ID NO:5]

```
5'- ATGAAACTCA AAGACACCCT TAATCTTGGG AAAACTGAAT TCCCAATGCG

TGCAGGCCTT CCTACCAAAG AGCCAGTTTG GCAAAAGGAA TGGGAAGATG

CAAAACTTTA TCAACGTCGT CAAGAATTGA ACCAAGGAAA ACCTCATTTC

ACCTTGCATG ATGGCCCTCC ATACGCTAAC GGAAATATCC ACGTTGGACA
```

TABLE 1-continued ileS Polynucleotide and Polypeptide Sequences

```
TGCTATGAAC AAGATTTCAA AAGATATCAT TGTTCGTTCT AAGTCTATGT

CAGGATTTTA CGCGCCATTT ATTCCTGGTT GGGATACTCA TGGTCTGCCA

ATCGAGCAAG TCTTGTCAAA ACAAGGTGTC AAACGTAAAG AAATGGACTT

GGTTGAGTAC TTGAAACTTT GCCGTGAGTA CGCTCTTTCT CAAGTAGATA

AACAACGTGA AGATTTTAAA CGTTTGGGTG TTTCTGGTGA CTGGGAAAAT

CCATATGTGA CCTTGACTCC TGACTATGAA GCAGCTCAAA TTCGTGTATT

TGGTGAGATG GCTAATAAGG GTTATATCTA CCGTGGTGCC AAGCCAGTTT

ACTGGTCATG GTCATCTGAG TCAGCCCTTG CTGAAGCAGA GATTGAATAC

CATGACTTGG TTTCAACTTC CCTTTACTAT GCCAACAAGG TAAAAGATGG

CAAAGGAGTT CTAGATACAG ATACTTATAT CGTTGTCTGG ACAACGACTC

CATTTACCAT CACAGCTTCT CGTGGTTTGA CGGTTGGTGC AGATATTGAT

TACGTTTTGG TTCAACCTGC TGGTGAAGCT CGTAAGTTTG TCGTTGCTGC

TGAATTATTG ACTAG-3'
```

Fragment 2 [SEQ ID NO:8]
```
5'- TTGTCTGAGA AATTTGGCTG GGCTGATGTT CAAGTTTTGG AAACTTACCG

TGGCCAAGAA CTTAACCACA TCGTAACAGA ACACCCATGG GATACAGCTG

TAGAAGAGTT GGTAATTCTT GGTGACCACG TTACGACTGA CTCTGGTACA

GGTATTGTCC ATACAGCCCC TGGTTTTGGT GAGGACGACT ACAATGTTGG

TATTGCTAAT AATCTTGAAG TCGCAGTGAC TGTTGATGAA CGTGGTATCA

TGATGAAGAA TGCTGGTCCT GAGTTTGAAG GTCAATTCTA TGAAAAGGTA

GTTCCAACTG TTATTGAAAA ACTTGGTAAC CTCCTTCTTG CCCAAGAAGA

AATCTCTCAC TCATATCCAT TGACTGGCG TACTAAGAAA CCAATCATCT

GGCGTGCAGT TCCACAATGG TTTGCCTCAG TTTCTAAATT CCGTCAAGAA

ATCTTGGACG AAATTGAAAA AGTGAAATTC CACTCAGAAT GGGGTAAAGT

CCGTCTTTAC AATATGATCC GTGACCGTGG TGACTGGGTT ATCTCTCGTC

AACGTGCTTG GGGTGTTCCA CTTCCAATCT TCTATGCAGA AGACGGTACA

GCTATCATGG TAGCTGAAAC GATTGAACAC GTAGCTCAAC TTTTTGAAGA

ACATGGTTCA AGCATTTGGT GGGAACGTGA TGCCAAAGAT CTCTTGCCAG

AAGGATTTAC TCATCCAGGT TCACCAAACG GCGAGTTCAA AAAAGAAACT

GATATCATGG ACGTTTGGTT TGACTCAGGT TCATCATGGA ATGGAGTGGT

GGTAAACCGT CCTGAATTGA CTTACCCAGC CGACCTTTAC CTAGAAGGTT

CTGACCAATA CCGTGGTTGG TTTAACTCAT CACTTATCAC ATCTGTTGCC

AACCATGGCG TAGCACCTTA CAAACAAATC TTGTCACAAG GTTTTGCCCT

TGATGGTAAA GGTGAGAAGA TGTCTAAATC TCTTGGAAAT ACCATTGCTC

CAAGCGATGT TGAAAAACAA TTCGGTGCTG AAATCTTGCG TCTCTGGGTA

ACAAGTGTTG ACTCAAGCAA TGACGTGCGT ATCTCTATGG ATATTTTGAG

CCAAGTTTCT GAAACTTACC GTAAGATTCG TAACACTCTT CGTTTCTTGA

TTGCCAATAC ATCTGACTTT AACCCAGCTC AAGATACAGT CGCTTACGAT

GAGCTTCGTT CAGTTGATAA GTACATGACG ATTCGCTTTA CCAGCTTGT
```

TABLE 1-continued ileS Polynucleotide and Polypeptide Sequences

```
          CAAGACCATT CGTGATGCCT ATGCAGACTT TGAATTCTTG ACGATCTACA

AGGCCTTGGT GAACTTTATC AACGTTGACT TGTCAGCCTT CTACCTTGAT

TTTGCCAAAG ATGTTGTTTA CATTGAAGGT GCCAAATCAC TGGAACGCCG

TCAAATGCAG ACTGTCTTCT ATGACATTCT TGTCAAAATC ACCAAACTCT

TGACACCAAT CCTTCCTCAC ACTGCGGAAG AAATTTGGTC ATATCTTGAG

TTTGAAACAG AAGACTTCGT CCAATTGTCA GAATTACCAG AGGCTCAAAC

TTTTGCTAAT CAAGAAGAAA TCTTGGATAC ATGGGCAGCC TTCATGGACT

TCCGTGGACA AGCTCAAAAA GCCTTGGAAG AAGCTCGTAA TGCAAAAGTA

ATCGGTAAAT CACTTGAAGC ACACTTGACA GTTTATCCAA ACGAAGTTGT

GAAAACTCTA CTCGAAGCAG TAAACAGCAA TGTGGCTCAA CTTTTGATCG

TGTCAGACTT GACCATCGCA GAAGGACCAG CTCCAGAAGC TGCCCTTAGC

TTCGAAGATG TAGCCTTCAC AGTTGAACGC GCTGCAGGTG AAGTATGTGA

CCGTTGCCGT CGTATTGACC CAACAACAGC AGAACGTAGC TACCAGGCAG

TTATCTGTGA CCACTGTGCA AGCATCGTAG AAGAAAACTT TGCGGAAGCA

GTCGCAGAAG GATTTGAAGA GAAATAA- 3'
```

(F) ileS polypeptide sequence deduced from the polynucleotide sequence of SEQ ID NO:5 [SEQ ID NO:6].

```
     NH2_ MKLKDTLNLG KTEFPMRAGL PTKEPVWQKE WEDAKLYQRR QELNQGKPHF

TLHDGPPYAN GNIHVGHAMN KISKDIIVRS KSMSGFYAPF IPGWDTHGLP

IEQVLSKQGV KRKEMDLVEY LKLCREYALS QVDKQREDFK RLGVSGDWEN

PYVTLTPDYE AAQIRVFGEM ANKGYIYRGA KPVYWSWSSE SALAEAEIEY

HDLVSTSLYY ANKVKDGKGV LDTDTYIVVW TTTPFTITAS RGLTVGADID

YVLVQPAGEA RKFVVAAELL T-COOH
``` ileS polypeptide sequence deduced from the polynucleotide sequence of SEQ ID NO:8 [SEQ ID NO:9].

```
     NH2_ LSEKFGWADY QVLETYRGQE LNHIVTEHPW DTAVEELVIL GDHVTTDSGT

GIVHTAPGFG EDDYNVGIAN NLEVAVTVDE RGIMMKNAGP EFEGQFYEKV

VPTVIEKLGN LLLAQEEISH SYPFDWRTKK PIIWRAVPQW FASVSKFRQE

ILDEIEKVKF HSEWGKVRLY NMIRDRGDWV ISRQRAWGVP LPIFYAEDGT

AIMVAETIEH VAQLFEEHGS SIWWERDAKD LLPEGFTHPG SPNGEFKKET

DIMDVWFDSG SSWNGVVVNR PELTYPADLY LEGSDQYRGW FNSSLITSVA

NHGVAPYKQI LSQGFALDGK GEKMSKSLGN TIAPSDVEKQ FGAEILRLWV

TSVDSSNDVR ISMDILSQVS ETYRKIRNTL RFLIANTSDF NPAQDTVAYD

ELRSVDKYMT IRFNQLVKTI RDAYADFEFL TIYKALVNFI NVDLSAFYLD

FAKDVVYIEG AKSLERRQMQ TVFYDILVKI TKLLTPILPH TAEEIWSYLE

FETEDFVQLS ELPEAQTFAN QEEILDTWAA FMDFRGQAQK ALEEARNAKV

IGKSLEAHLT VYPNEVVKTL LEAVNSNVAQ LLIVSDLTIA EGPAPEAALS

FEDVAFTVER AAGEVCDRCR RIDPTTAERS YQAVICDHCA SIVEENFAEA

VAEGFEEK-COOH
```

(G) Polynucleotide sequence embodiments.
    Fragent 1 [SEQ ID NO:5]
    X-(R$_1$)$_n$- ATGAAACTCA AAGACACCCT TAATCTTGGG AAAACTGAAT TCCCAATGCG

TABLE 1-continued ileS Polynucleotide and Polypeptide Sequences

```
         TGCAGGCCTT CCTACCAAAG AGCCAGTTTG GCAAAAGGAA TGGGAAGATG

CAAAACTTTA TCAACGTCGT CAAGAATTGA ACCAAGGAAA ACCTCATTTC

ACCTTGCATG ATGGCCCTCC ATACGCTAAC GGAAATATCC ACGTTGGACA

TGCTATGAAC AAGATTTCAA AAGATATCAT TGTTCGTTCT AAGTCTATGT

CAGGATTTTA CGCGCCATTT ATTCCTGGTT GGGATACTCA TGGTCTGCCA

ATCGAGCAAG TCTTGTCAAA ACAAGGTGTC AAACGTAAAG AAATGGACTT

GGTTGAGTAC TTGAAACTTT GCCGTGAGTA CGCTCTTTCT CAAGTAGATA

AACAACGTGA AGATTTTAAA CGTTTGGGTG TTTCTGGTGA CTGGGAAAAT

CCATATGTGA CCTTGACTCC TGACTATGAA GCAGCTCAAA TTCGTGTATT

TGGTGAGATG GCTAATAAGG GTTATATCTA CCGTGGTGCC AAGCCAGTTT

ACTGGTCATG GTCATCTGAG TCAGCCCTTG CTGAAGCAGA GATTGAATAC

CATGACTTGG TTTCAACTTC CCTTTACTAT GCCAACAAGG TAAAAGATGG

CAAAGGAGTT CTAGATACAG ATACTTATAT CGTTGTCTGG ACAACGACTC

CATTTACCAT CACAGCTTCT CGTGGTTTGA CGGTTGGTGC AGATATTGAT

TACGTTTTGG TTCAACCTGC TGGTGAAGCT CGTAAGTTTG TCGTTGCTGC

TGAATTATTG ACTAG-  (R₂)ₙ-Y
         Fragent 2 [SEQ ID NO:8]
X-(R₁)ₙ- TTGTCTGAGA AATTTGGCTG GGCTGATGTT CAAGTTTTGG AAACTTACCG

TGGCCAAGAA CTTAACCACA TCGTAACAGA ACACCCATGG GATACAGCTG

TAGAAGAGTT GGTAATTCTT GGTGACCACG TTACGACTGA CTCTGGTACA

GGTATTGTCC ATACAGCCCC TGGTTTTGGT GAGGACGACT ACAATGTTGG

TATTGCTAAT AATCTTGAAG TCGCAGTGAC TGTTGATGAA CGTGGTATCA

TGATGAAGAA TGCTGGTCCT GAGTTTGAAG GTCAATTCTA TGAAAAGGTA

GTTCCAACTG TTATTGAAAA ACTTGGTAAC CTCCTTCTTG CCCAAGAAGA

AATCTCTCAC TCATATCCAT TTGACTGGCG TACTAAGAAA CCAATCATCT

GGCGTGCAGT TCCACAATGG TTTGCCTCAG TTTCTAAATT CCGTCAAGAA

ATCTTGGACG AAATTGAAAA AGTGAAATTC CACTCAGAAT GGGGTAAAGT

CCGTCTTTAC AATATGATCC GTGACCGTGG TGACTGGGTT ATCTCTCGTC

AACGTGCTTG GGGTGTTCCA CTTCCAATCT TCTATGCAGA AGACGGTACA

GCTATCATGG TAGCTGAAAC GATTGAACAC GTAGCTCAAC TTTTTGAAGA

ACATGGTTCA AGCATTTGGT GGGAACGTGA TGCCAAAGAT CTCTTGCCAG

AAGGATTTAC TCATCCAGGT TCACCAAACG GCGAGTTCAA AAAAGAAACT

GATATCATGG ACGTTTGGTT TGACTCAGGT TCATCATGGA ATGGAGTGGT

GGTAAACCGT CCTGAATTGA CTTACCCAGC CGACCTTTAC CTAGAAGGTT

CTGACCAATA CCGTGGTTGG TTTAACTCAT CACTTATCAC ATCTGTTGCC

AACCATGGCG TAGCACCTTA CAAACAAATC TTGTCACAAG GTTTTGCCCT

TGATGGTAAA GGTGAGAAGA TGTCTAAATC TCTTGGAAAT ACCATTGCTC

CAAGCGATGT TGAAAAACAA TTCGGTGCTG AAATCTTGCG TCTCTGGGTA

ACAAGTGTTG ACTCAAGCAA TGACGTGCGT ATCTCTATGG ATATTTTGAG
```

TABLE 1-continued ileS Polynucleotide and Polypeptide Sequences

```
           CCAAGTTTCT GAAACTTACC GTAAGATTCG TAACACTCTT CGTTTCTTGA

TTGCCAATAC ATCTGACTTT AACCCAGCTC AAGATACAGT CGCTTACGAT

GAGCTTCGTT CAGTTGATAA GTACATGACG ATTCGCTTTA ACCAGCTTGT

CAAGACCATT CGTGATGCCT ATGCAGACTT TGAATTCTTG ACGATCTACA

AGGCCTTGGT GAACTTTATC AACGTTGACT TGTCAGCCTT CTACCTTGAT

TTTGCCAAAG ATGTTGTTTA CATTGAAGGT GCCAAATCAC TGGAACGCCG

TCAAATGCAG ACTGTCTTCT ATGACATTCT TGTCAAAATC ACCAAACTCT

TGACACCAAT CCTTCCTCAC ACTGCGGAAG AAATTTGGTC ATATCTTGAG

TTTGAAACAG AAGACTTCGT CCAATTGTCA GAATTACCAG AGGCTCAAAC

TTTTGCTAAT CAAGAAGAAA TCTTGGATAC ATGGGCAGCC TTCATGGACT

TCCGTGGACA AGCTCAAAAA GCCTTGGAAG AAGCTCGTAA TGCAAAAGTA

ATCGGTAAAT CACTTGAAGC ACACTTGACA GTTTATCCAA ACGAAGTTGT

GAAAACTCTA CTCGAAGCAG TAAACAGCAA TGTGGCTCAA CTTTTGATCG

TGTCAGACTT GACCATCGCA GAAGGACCAG CTCCAGAAGC TGCCCTTAGC

TTCGAAGATG TAGCCTTCAC AGTTGAACGC GCTGCAGGTG AAGTATGTGA

CCGTTGCCGT CGTATTGACC AACAACAGC AGAACGTAGC TACCAGGCAG

TTATCTGTGA CCACTGTGCA AGCATCGTAG AAGAAAACTT TGCGGAAGCA

GTCGCAGAAG GATTTGAAGA GAAATAA-(R₂)ₙ-Y
```

(H) Polypeptide sequence embodiments [SEQ ID NO:6].

```
 X-(R₁)ₙ-  MKLKDTLNLG KTEFPMRAGL PTKEPVWQKE WEDAKLYQRR QELNQGKPHF

TLHDGPPYAN GNIHVGHAMN KISKDIIVRS KSMSGFYAPF IPGWDTHGLP

IEQVLSKQGV KRKEMDLVEY LKLCREYALS QVDKQREDFK RLGVSGDWEN

PYVTLTPDYE AAQIRVFGEM ANKGYIYRGA KPVYWSWSSE SALAEAEIEY

HDLVSTSLYY ANKVKDGKGV LDTDTYIVVW TTTPFTITAS RGLTVGADID

YVLVQPAGEA RKFVVAAELL T-(R₂)ₙ₋ᵧ

[SEQ ID NO:9]
 X-(R₁)ₙ-  LSEKFGWADV QVLETYRGQE LNHIVTEHPW DTAVEELVIL GDHVTTDSGT

GIVHTAPGFG EDDYNVGIAN NLEVAVTVDE RGIMMKNAGP EFEGQFYEKV

VPTVIEKLGN LLLAQEEISH SYPFDWRTKK PIIWRAVPQW FASVSKFRQE

ILDEIEKVKF HSEWGKVRLY NMIRDRGDWV ISRQRAWGVP LPIFYAEDGT

AIMVAETIEH VAQLFEEHGS SIWWERDAKD LLPEGFTHPG SPNGEFKKET

DIMDVWFDSG SSWNGVVVNR PELTYPADLY LEGSDQYRGW FNSSLITSVA

NHGVAPYKQI LSQGFALDGK GEKMSKSLGN TIAPSDVEKQ FGAEILRLWV

TSVDSSNDVR ISMDILSQVS ETYRKIRNTL RFLIANTSDF NPAQDTVAYD

ELRSVDKYMT IRFNQLVKTI RDAYADFEFL TIYKALVNFI NVDLSAFYLD

FAKDVVYIEG AKSLERRQMQ TVFYDILVKI TKLLTPILPH TAEETWSYLE

FETEDFVQLS ELPEAQTFAN QEEILDTWAA FMDFRGQAQK ALEEARNAKV

IGKSLEAHLT VYPNEVVKTL LEAVNSNVAQ LLIVSDLTIA EGPAPEAALS

FEDVAFTVER AAGEVCDRCR RIDPTTAERS YQAVICDHCA SIVEENFAEA

VAEGFEEK- (R₂)ₙ-Y
```

TABLE 1-continued ileS Polynucleotide and Polypeptide Sequences (I) Polynucleotide sequence embodiment [SEQ ID NO:10].

```
5'- CAACTTTTTG AAGAACATGG TTCAAGCATT TGGTGGGAAC GTGATGCCAA
    AGATCTCTTG CCAGAAGGAT TTACTCATCC AGGTTCACCA AACGGCGAGT

TCAAAAAAGA AACTGATATC ATGGACGTTT GGTTTGACTC AGGTTCATCA

TGGAATGGAG TGGTGGTAAA CCGTCCTGAA TTGACTTACC CAGCCGACCT

TTACCTAGAA GGTTCTGACC AATACCGTGG TTGGTTTAAC TCATCACTTA

TCACATCTGT TGCCAACCAT GGCGTAGCAC CTTACAAACA AATCTTGTCA

CAAGGTTTTG CCCTTGATGG TAAAGGTGAG AAGATGTCTA AATCTCTTGG

AAATACCATT GCTCCAAGCG ATGTTGAAAA ACAATTCGGG-3'
```

Deposited materials

A deposit containing a *Streptococcus pneumoniae* 0100993 strain has been deposited with the National Collections of Industrial and Marine Bacteria Ltd. (herein "NCIMB"), 23 St. Machar Drive, Aberdeen AB2 1RY, Scotland on Apr. 11, 1996 and assigned deposit number 40794. The deposit was described as *Streptococcus peumnoniae* 0100993 on deposit. On Apr. 17, 1996 a *Streptococcus peumnoniae* 0100993 DNA library in *E. coli* was similarly deposited with the NCIMB and assigned deposit number 40800. The *Streptococcus pneumoniae* strain deposit is referred to herein as "the deposited strain" or as "the DNA of the deposited strain."

The deposited strain contains the full length ileS gene. The sequence of the polynucleotides contained in the deposited strain, as well as the amino acid sequence of the polypeptide encoded thereby, are controlling in the event of any conflict with any description of sequences herein.

The deposit of the deposited strain has been made under the terms of the Budapest Treaty on the International Recognition of the Deposit of Micro-organisms for Purposes of Patent Procedure. The strain will be irrevocably and without restriction or condition released to the public upon the issuance of a patent. The deposited strain is provided merely as convenience to those of skill in the art and is not an admission that a deposit is required for enablement, such as that required under 35 U.S.C. §112.

A license may be required to make, use or sell the deposited strain, and compounds derived therefrom, and no such license is hereby granted.

Polypeptides

The polypeptides of the invention include the polypeptide of Table 1 [SEQ ID NO: 2, 6 and 9] (in particular the mature polypeptide) as well as polypeptides and fragments, particularly those which have the biological activity of ileS, and also those which have at least 70% identity to the polypeptide of Table 1 [SEQ ID NO: 2, 6 and 9] or the relevant portion, preferably at least 80% identity to the polypeptide of Table 1 [SEQ ID NO: 2, 6 and 9], and more preferably at least 90% similarity (more preferably at least 90% identity) to the polypeptide of Table 1 [SEQ ID NO: 2, 6 and 9] and still more preferably at least 95% similarity (still more preferably at least 95% identity) to the polypeptide of Table 1 [SEQ ID NO: 2, 6 and 9] and also include portions of such polypeptides with such portion of the polypeptide generally containing at least 30 amino acids and more preferably at least 50 amino acids.

The invention also includes polypeptides of the formula set forth in Table 1 (D) wherein, at the amino terminus, X is hydrogen, and at the carboxyl terminus, Y is hydrogen or a metal, $R_1$ and $R_2$ is any amino acid residue, and n is an integer between 1 and 1000 or 2000. Any stretch of amino acid residues denoted by either R group, where n is an integer grater than 1, may be either a heteropolymer or a homopolymer, preferably a heteropolymer.

The invention also includes polypeptides of the formula set forth in Table 1 (H) wherein, at the amino terminus, X is hydrogen, and at the carboxyl terminus, Y is hydrogen or a metal, $R_1$ and $R_2$ is any amino acid residue, and n is an integer between 1 and 1000. Any stretch of amino acid residues denoted by either R group, where R is greater than 1, may be either a heteropolymer or a homopolymer, preferably a heteropolymer.

A fragment is a variant polypeptide having an amino acid sequence that entirely is the same as part but not all of the amino acid sequence of the aforementioned polypeptides. As with ileS polypeptides fragments may be "free-standing," or comprised within a larger polypeptide of which they form a part or region, most preferably as a single continuous region, a single larger polypeptide.

Preferred fragments include, for example, truncation polypeptides having a portion of the amino acid sequence of Table 1 [SEQ ID NO: 2, 6 and 9], or of variants thereof, such as a continuous series of residues that includes the amino terminus, or a continuous series of residues that includes the carboxyl terminus. Degradation forms of the polypeptides of the invention in a host cell, particularly a *Streptococcus pneumoniae*, are also preferred. Further preferred are fragments characterized by structural or functional attributes such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions.

Also preferred are biologically active fragments which are those fragments that mediate activities of ileS, including those with a similar activity or an improved activity, or with a decreased undesirable activity. Also included are those fragments that are antigenic or immunogenic in an animal, especially in a human. Particularly preferred are fragments comprising receptors or domains of enzymes that confer a function essential for viability of *Streptococcus pneumoniae* or the ability to initiate, or maintain cause disease in an individual, particularly a human.

Variants that are fragments of the polypeptides of the invention may be employed for producing the corresponding full-length polypeptide by peptide synthesis; therefore, these variants may be employed as intermediates for producing the full-length polypeptides of the invention.

Polynucleotides

Another aspect of the invention relates to isolated polynucleotides, including the full length gene, that encode the ileS polypeptide having the deduced amino acid sequence of Table 1 [SEQ ID NO: 2, 6 and 9] and polynucleotides closely related thereto and variants thereof.

Using the information provided herein, such as the polynucleotide sequence set out in Table 1 [SEQ ID NO: 1, 5, 8 and 10], a polynucleotide of the invention encoding ileS polypeptide may be obtained using standard cloning and screening methods, such as those for cloning and sequencing chromosomal DNA fragments from bacteria using *Streptococcus pneumoniae* 0100993 cells as starting material, followed by obtaining a full length clone. For example, to obtain a polynucleotide sequence of the invention, such as the sequence given in Table 1 [SEQ ID NO: 1, 5, 8 and 10], typically a library of clones of chromosomal DNA of *Streptococcus pneumoniae* 0100993 in *E.coli* or some other suitable host is probed with a radiolabeled oligonucleotide, preferably a 17-mer or longer, derived from a partial sequence. Clones carrying DNA identical to that of the probe can then be distinguished using stringent conditions. By sequencing the individual clones thus identified with sequencing primers designed from the original sequence it is then possible to extend the sequence in both directions to determine the full gene sequence. Conveniently, such sequencing is performed using denatured double stranded DNA prepared from a plasmid clone. Suitable techniques are described by Maniatis, T., Fritsch, E. F. and Sambrook et al., *MOLECULAR CLONING, A LABORATORY MANUAL*, 2nd Ed.; Cold Spring Harbor Laboratory Press, Cold Spring Harbor, N.Y. (1989). (see in particular Screening By Hybridization 1.90 and Sequencing Denatured Double-Stranded DNA Templates 13.70). Illustrative of the invention, the polynucleotide set out in Table 1 [SEQ ID NO: 1, 5, 8 and 10] was discovered in a DNA library derived from *Streptococcus pneumoniae* 0100993.

The DNA sequence set out in Table 1 [ SEQ ID NO: 1, 5, 8 and 10] contains an open reading frame encoding a protein having about the number of amino acid residues set forth in Table 1 [SEQ ID NO: 2, 6 and 9] with a deduced molecular weight that can be calculated using amino acid residue molecular weight values well known in the art. The polynucleotide of SEQ ID NO: 1, between nucleotide number 1 through number 2790 encodes the polypeptide of SEQ ID NO: 2. The stop codon begins at nucleotide number 2791 of SEQ ID NO: 1.

The other DNA sequences set out in Table 1 as SEQ ID NOS: 5 and 8 contain open reading frames encoding a protein having about the number of amino acid residues set forth in Table 1 as SEQ ID NO: 6 and 9, respectively, with a deduced molecular weight that can be calculated using amino acid residue molecular weight values well known in the art. The start codon of the DNA in Table 1 is nucleotide number 1 and last codon that encodes an amino acid is number 815 for "Fragment 1" herein, and analogously 1 to 1974 for "Fragment 2" herein, the stop codon being the next codon following this last codon encoding an amino acid.

ileS of the invention is structurally related to other proteins of the isoleucyl tRNA synthetase family, as shown by the results of sequencing the DNA encoding ileS of the deposited strain. The protein exhibits greatest homology to *Staphylococcus aureus* isoleucyl tRNA synthetase protein among known proteins. ileS of Table 1 [SEQ ID NO: 2, 6 and 9] has about 55% identity over its entire length and about 71% similarity over its entire length with the amino acid sequence of *Staphylococcus aureus* isoleucyl tRNA synthetase polypeptide.

The invention provides a polynucleotide sequence identical over its entire length to the coding sequence in Table 1 [SEQ ID NO: 1, 5, 8 and 10]. Also provided by the invention is the coding sequence for the mature polypeptide or a fragment thereof, by itself as well as the coding sequence for the mature polypeptide or a fragment in reading frame with other coding sequence, such as those encoding a leader or secretory sequence, a pre-, or pro or prepro-protein sequence. The polynucleotide may also contain non-coding sequences, including for example, but not limited to non-coding 5' and 3' sequences, such as the transcribed, non-translated sequences, termination signals, ribosome binding sites, sequences that stabilize mRNA, introns, polyadenylation signals, and additional coding sequence which encode additional amino acids. For example, a marker sequence that facilitates purification of the fused polypeptide can be encoded. In certain embodiments of the invention, the marker sequence is a hexa-histidine peptide, as provided in the pQE vector (Qiagen, Inc.) and described in Gentz et al., *Proc. Natl. Acad. Sci., USA* 86: 821–824 (1989), or an HA tag (Wilson et al., *Cell* 37: 767 (1984). Polynucleotides of the invention also include, but are not limited to, polynucleotides comprising a structural gene and its naturally associated sequences that control gene expression.

A preferred embodiment of the invention is the polynucleotide of comprising nucleotide 1 to 2790 set forth in SEQ ID NO: 1 of Table 1 which encodes the ileS polypeptide.

Another preferred embodiment of the invention includes, for example, a polynucleotide comprising nucleotide 1 to 815 or 1 to 1974 set forth in SEQ ID NO: 5 and SEQ ID NO: 8 respectively of Table 1 each of which encodes ileS polypeptide.

The invention also includes polynucleotides of the formula set forth in Table 1 (C) wherein, at the 5' end of the molecule, X is hydrogen, and at the 3' end of the molecule, Y is hydrogen or a metal, $R_1$ and $R_2$ is any nucleic acid residue, and n is an integer between 1 and 1000, 2000 or 3000. Any stretch of nucleic acid residues denoted by either R group, where R is greater than 1, may be either a heteropolymer or a homopolymer, preferably a heteropolymer.

The invention also includes polynucleotides of the formula set forth in Table 1 (G) wherein, at the 5' end of the molecule, X is hydrogen, and at the 3' end of the molecule, Y is hydrogen or a metal, $R_1$ and $R_2$ is any nucleic acid residue, and n is an integer between 1 and 1000. Any stretch of nucleic acid residues denoted by either R group, where R is greater than 1, may be either a heteropolymer or a homopolymer, preferably a heteropolymer.

The term "polynucleotide encoding a polypeptide" as used herein encompasses polynucleotides that include a sequence encoding a polypeptide of the invention, particularly a bacterial polypeptide and more particularly a polypeptide of the *Streptococcus pneumoniae* ileS having the amino acid sequence set out in Table 1 [SEQ ID NO: 2, 6 and 9]. The term also encompasses polynucleotides that include a single continuous region or discontinuous regions encoding the polypeptide (for example, interrupted by integrated phage or an insertion sequence or editing) together with additional regions, that also may contain coding and/or non-coding sequences.

The invention further relates to variants of the polynucleotides described herein that encode for variants of the polypeptide having the deduced amino acid sequence of Table 1 [SEQ ID NO: 2, 6 and 9]. Variants that are fragments of the polynucleotides of the invention may be used to synthesize full-length polynucleotides of the invention.

Further particularly preferred embodiments are polynucleotides encoding ileS variants, that have the amino acid sequence of ileS polypeptide of Table 1 [SEQ ID NO: 2, 6 and 9] in which several, a few, 5 to 10, 1 to 5, 1 to 3, 2, 1 or no amino acid residues are substituted, deleted or added, in any combination. Especially preferred among these are silent substitutions, additions and deletions, that do not alter the properties and activities of ileS.

Further preferred embodiments of the invention are polynucleotides that are at least 70% identical over their entire length to a polynucleotide encoding ileS polypeptide having the amino acid sequence set out in Table 1 [SEQ ID NO: 2, 6 and 9], and polynucleotides that are complementary to such polynucleotides. Alternatively, most highly preferred are polynucleotides that comprise a region that is at least 80% identical over its entire length to a polynucleotide encoding ileS polypeptide of the deposited strain and polynucleotides complementary thereto. In this regard, polynucleotides at least 90% identical over their entire length to the same are particularly preferred, and among these particularly preferred polynucleotides, those with at least 95% are especially preferred. Furthermore, those with at least 97% are highly preferred among those with at least 95%, and among these those with at least 98% and at least 99% are particularly highly preferred, with at least 99% being the more preferred.

Preferred embodiments are polynucleotides that encode polypeptides that retain substantially the same biological function or activity as the mature polypeptide encoded by the DNA of Table 1 [SEQ ID NO: 1, 5, 8 and 10].

The invention further relates to polynucleotides that hybridize to the herein above-described sequences. In this regard, the invention especially relates to polynucleotides that hybridize under stringent conditions to the herein above-described polynucleotides. As herein used, the terms "stringent conditions" and "stringent hybridization conditions" mean hybridization will occur only if there is at least 95% and preferably at least 97% identity between the sequences. An example of stringent hybridization conditions is overnight incubation at 42° C. in a solution comprising: 50% formamide, 5×SSC (150 mM NaCl, 15 mM trisodium citrate), 50 mM sodium phosphate (pH7.6), 5×Denhardt's solution, 10% dextran sulfate, and 20 micrograms/ml denatured, sheared salmon sperm DNA, followed by washing the hybridization support in 0.1×SSC at about 65° C. Hybridization and wash conditions are well known and exemplified in Sambrook, et al., *Molecular Cloning: A Laboratory Manual*, Second Edition, Cold Spring Harbor, N.Y., (1989), particularly Chapter 11 therein.

The invention also provides a polynucleotide consisting essentially of a polynucleotide sequence obtainable by screening an appropriate library containing the complete gene for a polynucleotide sequence set forth in SEQ ID NO: 1, 5, 8 and 10 under stringent hybridization conditions with a probe having the sequence of said polynucleotide sequence set forth in SEQ ID NO: 1, 5, 8 and 10 or a fragment thereof; and isolating said DNA sequence. Fragments useful for obtaining such a polynucleotide include, for example, probes and primers described elsewhere herein.

As discussed additionally herein regarding polynucleotide assays of the invention, for instance, polynucleotides of the invention as discussed above, may be used as a hybridization probe for RNA, cDNA and genomic DNA to isolate full-length cDNAs and genomic clones encoding ileS and to isolate cDNA and genomic clones of other genes that have a high sequence similarity to the ileS gene. Such probes generally will comprise at least 15 bases. Preferably, such probes will have at least 30 bases and may have at least 50 bases. Particularly preferred probes will have at least 30 bases and will have 50 bases or less.

For example, the coding region of the ileS gene may be isolated by screening using the DNA sequence provided in SEQ ID NO: 1 to synthesize an oligonucleotide probe. A labeled oligonucleotide having a sequence complementary to that of a gene of the invention is then used to screen a library of cDNA, genomic DNA or mRNA to determine which members of the library the probe hybridizes to.

The polynucleotides and polypeptides of the invention may be employed, for example, as research reagents and materials for discovery of treatments of and diagnostics for disease, particularly human disease, as further discussed herein relating to polynucleotide assays.

Polynucleotides of the invention that are oligonucleotides derived from the sequences of SEQ ID NOS: 1 and/or 2 and/or 5 and/or 6 and/or 8 and/or 9 and/or 10 may be used in the processes herein as described, but preferably for PCR, to determine whether or not the polynucleotides identified herein in whole or in part are transcribed in bacteria in infected tissue. It is recognized that such sequences will also have utility in diagnosis of the stage of infection and type of infection the pathogen has attained.

The invention also provides polynucleotides that may encode a polypeptide that is the mature protein plus additional amino or carboxyl-terminal amino acids, or amino acids interior to the mature polypeptide (when the mature form has more than one polypeptide chain, for instance). Such sequences may play a role in processing of a protein from precursor to a mature form, may allow protein transport, may lengthen or shorten protein half-life or may facilitate manipulation of a protein for assay or production, among other things. As generally is the case in vivo, the additional amino acids may be processed away from the mature protein by cellular enzymes.

A precursor protein, having the mature form of the polypeptide fused to one or more prosequences may be an inactive form of the polypeptide. When prosequences are removed such inactive precursors generally are activated. Some or all of the prosequences may be removed before activation. Generally, such precursors are called proproteins.

In sum, a polynucleotide of the invention may encode a mature protein, a mature protein plus a leader sequence (which may be referred to as a preprotein), a precursor of a mature protein having one or more prosequences that are not the leader sequences of a preprotein, or a preproprotein, which is a precursor to a proprotein, having a leader sequence and one or more prosequences, which generally are removed during processing steps that produce active and mature forms of the polypeptide.

Vectors, host cells, expression

The invention also relates to vectors that comprise a polynucleotide or polynucleotides of the invention, host cells that are genetically engineered with vectors of the invention and the production of polypeptides of the invention by recombinant techniques. Cell-free translation systems can also be employed to produce such proteins using RNAs derived from the DNA constructs of the invention.

For recombinant production, host cells can be genetically engineered to incorporate expression systems or portions thereof or polynucleotides of the invention. Introduction of a polynucleotide into the host cell can be effected by methods described in many standard laboratory manuals, such as Davis et al., BASIC METHODS IN MOLECULAR BIOLOGY, (1986) and Sambrook et al., MOLECULAR CLONING: A LABORATORY MANUAL, 2nd Ed., Cold Spring Harbor Laboratory Press, Cold Spring Harbor, N.Y. (1989), such as, calcium phosphate transfection, DEAE-dextran mediated transfection, transvection, microinjection, cationic lipid-mediated transfection, electroporation, transduction, scrape loading, ballistic introduction and infection.

Representative examples of appropriate hosts include bacterial cells, such as streptococci, staphylococci, enterococci E. coli, streptomyces and Bacillus subtilis cells; fungal cells, such as yeast cells and Aspergillus cells; insect cells such as Drosophila S2 and Spodoptera Sf9 cells; animal cells such as CHO, COS, HeLa, C127, 3T3, BHK, 293 and Bowes melanoma cells; and plant cells.

A great variety of expression systems can be used to produce the polypeptides of the invention. Such vectors include, among others, chromosomal, episomal and virus-derived vectors, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression system constructs may contain control regions that regulate as well as engender expression. Generally, any system or vector suitable to maintain, propagate or express polynucleotides and/or to express a polypeptide in a host may be used for expression in this regard. The appropriate DNA sequence may be inserted into the expression system by any of a variety of well-known and routine techniques, such as, for example, those set forth in Sambrook et al., MOLECULAR CLONING, A LABORATORY MANUAL, (supra).

For secretion of the translated protein into the lumen of the endoplasmic reticulum, into the periplasmic space or into the extracellular environment, appropriate secretion signals may be incorporated into the expressed polypeptide. These signals may be endogenous to the polypeptide or they may be heterologous signals.

Polypeptides of the invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography, and lectin chromatography. Most preferably, high performance liquid chromatography is employed for purification. Well known techniques for refolding protein may be employed to regenerate active conformation when the polypeptide is denatured during isolation and or purification.

Diagnostic Assays

This invention is also related to the use of the ileS polynucleotides of the invention for use as diagnostic reagents. Detection of ileS in a eukaryote, particularly a mammal, and especially a human, will provide a diagnostic method for diagnosis of a disease. Eukaryotes (herein also "individual(s)"), particularly mammals, and especially humans, particularly those infected or suspected to be infected with an organism comprising the ileS gene may be detected at the nucleic acid level by a variety of techniques.

Nucleic acids for diagnosis may be obtained from an infected individual's cells and tissues, such as bone, blood, muscle, cartilage, and skin. Genomic DNA may be used directly for detection or may be amplified enzymatically by using PCR or other amplification technique prior to analysis. RNA or cDNA may also be used in the same ways. Using amplification, characterization of the species and strain of prokaryote present in an individual, may be made by an analysis of the genotype of the prokaryote gene. Deletions and insertions can be detected by a change in size of the amplified product in comparison to the genotype of a reference sequence. Point mutations can be identified by hybridizing amplified DNA to labeled ileS polynucleotide sequences. Perfectly matched sequences can be distinguished from mismatched duplexes by RNase digestion or by differences in melting temperatures. DNA sequence differences may also be detected by alterations in the electrophoretic mobility of the DNA fragments in gels, with or without denaturing agents, or by direct DNA sequencing. See, e.g., Myers et al., Science, 230: 1242 (1985). Sequence changes at specific locations also may be revealed by nuclease protection assays, such as RNase and S1 protection or a chemical cleavage method. See, e.g., Cotton et al., Proc. Natl. Acad Sci., USA, 85: 4397–4401 (1985).

Cells carrying mutations or polymorphisms in the gene of the invention may also be detected at the DNA level by a variety of techniques, to allow for serotyping, for example. For example, RT-PCR can be used to detect mutations. It is particularly preferred to used RT-PCR in conjunction with automated detection systems, such as, for example, GeneScan. RNA or cDNA may also be used for the same purpose, PCR or RT-PCR. As an example, PCR primers complementary to a nucleic acid encoding ileS can be used to identify and analyze mutations. Examples of representative primers are shown below in Table 2.

TABLE 2

Primers for amplification of ileS polynucleotides

| SEQ ID NO | PRIMER SEQUENCE |
|---|---|
| 3 | 5'-ATGAAACTTCAAAGACACCCTTAAT-3' |
| 4 | 5'-TTATTTCTCTCAAATCCTTCTGC-3' |

The invention further provides these primers with 1, 2, 3 or 4 nucleotides removed from the 5' and/or the 3' end. These primers may be used for, among other things, amplifying ileS DNA isolated from a sample derived from an individual. The primers may be used to amplify the gene isolated from an infected individual such that the gene may then be subject to various techniques for elucidation of the DNA sequence. In this way, mutations in the DNA sequence may be detected and used to diagnose infection and to serotype and/or classify the infectious agent.

The invention further provides a process for diagnosing, disease, preferably bacterial infections, more preferably infections by Streptococcus pneumoniae, and most preferably otitis media, conjunctivitis, pneumonia, bacteremia, meningitis, sinusitis, pleural empyema and endocarditis, and most particularly meningitis, such as for example infection of cerebrospinal fluid, comprising determining from a sample derived from an individual a increased level of expression of polynucleotide having the sequence of Table 1 [SEQ ID NO: 1]. Increased or decreased expression of ileS polynucleotide can be measured using any on of the methods well known in the art for the quantation of polynucleotides, such as, for example, amplification, PCR, RT-PCR, RNase protection, Northern blotting and other hybridization methods.

In addition, a diagnostic assay in accordance with the invention for detecting over-expression of ileS protein compared to normal control tissue samples may be used to detect the presence of an infection, for example. Assay techniques that can be used to determine levels of a ileS protein, in a sample derived from a host are well-known to those of skill in the art. Such assay methods include radioimmunoassays, competitive-binding assays, Western Blot analysis and ELISA assays.

Antibodies

The polypeptides of the invention or variants thereof, or cells expressing them can be used as an immunogen to produce antibodies immunospecific for such polypeptides. "Antibodies" as used herein includes monoclonal and polyclonal antibodies, chimeric, single chain, simianized antibodies and humanized antibodies, as well as Fab fragments, including the products of an Fab immunolglobulin expression library.

Antibodies generated against the polypeptides of the invention can be obtained by administering the polypeptides or epitope-bearing fragments, analogues or cells to an animal, preferably a nonhuman, using routine protocols. For preparation of monoclonal antibodies, any technique known in the art that provides antibodies produced by continuous cell line cultures can be used. Examples include various techniques, such as those in Kohler, G. and Milstein, C., Nature 256: 495–497 (1975); Kozbor et al., Immunology Today 4: 72 (1983); Cole et al., pg. 77–96 in MONOCLONAL ANTIBODIES AND CANCER THERAPY, Alan R. Liss, Inc. (1985).

Techniques for the production of single chain antibodies (U.S. Pat. No. 4,946,778) can be adapted to produce single chain antibodies to polypeptides of this invention. Also, transgenic mice, or other organisms such as other mammals, may be used to express humanized antibodies.

Alternatively phage display technology may be utilized to select antibody genes with binding activities towards the polypeptide either from repertoires of PCR amplified v-genes of lymphocytes from humans screened for possessing anti-ileS or from naive libraries (McCafferty, J. et al., (1990), Nature 348, 552–554; Marks, J. et al., (1992) Biotechnology 10, 779–783). The affinity of these antibodies can also be improved by chain shuffling (Clackson, T. et al., (1991) Nature 352, 624–628).

If two antigen binding domains are present each domain may be directed against a different epitope—termed 'bispecific' antibodies.

The above-described antibodies may be employed to isolate or to identify clones expressing the polypeptides to purify the polypeptides by affinity chromatography.

Thus, among others, antibodies against ileS- polypeptide may be employed to treat infections, particularly bacterial infections and especially otitis media, conjunctivitis, pneumonia, bacteremia, meningitis, sinusitis, pleural empyema and endocarditis, and most particularly meningitis, such as for example infection of cerebrospinal fluid.

Polypeptide variants include antigenically, epitopically or immunologically equivalent variants that form a particular aspect of this invention. The term "antigenically equivalent derivative" as used herein encompasses a polypeptide or its equivalent which will be specifically recognized by certain antibodies which, when raised to the protein or polypeptide according to the invention, interfere with the immediate physical interaction between pathogen and mammalian host. The term "immunologically equivalent derivative" as used herein encompasses a peptide or its equivalent which when used in a suitable formulation to raise antibodies in a vertebrate, the antibodies act to interfere with the immediate physical interaction between pathogen and mammalian host.

The polypeptide, such as an antigenically or immunologically equivalent derivative or a fusion protein thereof is used as an antigen to immunize a mouse or other animal such as a rat or chicken. The fusion protein may provide stability to the polypeptide. The antigen may be associated, for example by conjugation, with an immunogenic carrier protein for example bovine serum albumin (BSA) or keyhole limpet haemocyanin (KLH). Alternatively a multiple antigenic peptide comprising multiple copies of the protein or polypeptide, or an antigenically or immunologically equivalent polypeptide thereof may be sufficiently antigenic to improve immunogenicity so as to obviate the use of a carrier.

Preferably, the antibody or variant thereof is modified to make it less immunogenic in the individual. For example, if the individual is human the antibody may most preferably be "humanized"; where the complimentarity determining region(s) of the hybridoma-derived antibody has been transplanted into a human monoclonal antibody, for example as described in Jones, P. et al. (1986), Nature 321, 522–525 or Tempest et al.,(1991) Biotechnology 9, 266–273.

The use of a polynucleotide of the invention in genetic immunization will preferably employ a suitable delivery method such as direct injection of plasmid DNA into muscles (Wolff et al., Hum Mol Genet 1992, 1:363, Manthorpe et al., Hum. Gene Ther. 1963:4, 419), delivery of DNA complexed with specific protein carriers (Wu et al., J. Biol Chem. 1989: 264,16985), coprecipitation of DNA with calcium phosphate (Benvenisty & Reshef, PNAS USA, 1986:83,9551), encapsulation of DNA in various forms of liposomes (Kaneda et al., Science 1989:243,375), particle bombardment (Tang et al., Nature 1992, 356:152, Eisenbraun et al., DNA Cell Biol 1993, 12:791) and in vivo infection using cloned retroviral vectors (Seeger et al., PNAS USA 1984:81,5849).

Antagonists and agonists—assays and molecules

Polypeptides of the invention may also be used to assess the binding of small molecule substrates and ligands in, for example, cells, cell-free preparations, chemical libraries, and natural product mixtures. These substrates and ligands may be natural substrates and ligands or may be structural or functional mimetics. See, e.g., Coligan et al., Current Protocols in Immunology 1(2): Chapter 5 (1991).

The invention also provides a method of screening compounds to identify those which enhance (agonist) or block (antagonist) the action of ileS polypeptides or polynucleotides, particularly those compounds that are bacteriostatic and/or bactericidal. The method of screening may involve high-throughput techniques. For example, to screen for agonists or antagonists, a synthetic reaction mix, a cellular compartment, such as a membrane, cell envelope or cell wall, or a preparation of any thereof, comprising ileS polypeptide and a labeled substrate or ligand of such polypeptide is incubated in the absence or the presence of a candidate molecule that may be a ileS agonist or antagonist. The ability of the candidate molecule to agonize or antagonize the ileS polypeptide is reflected in decreased binding of the labeled ligand or decreased production of product from such substrate. Molecules that bind gratuitously, i.e., without inducing the effects of ileS polypeptide are most likely to be good antagonists. Molecules that bind well and increase the rate of product production from substrate are agonists. Detection of the rate or level of production of product from substrate may be enhanced by using a reporter system. Reporter systems that may be useful in this regard include but are not limited to colorimetric labeled substrate converted into product, a reporter gene that is responsive to changes in ileS polynucleotide or polypeptide activity, and binding assays known in the art.

Another example of an assay for ileS antagonists is a competitive assay that combines ileS and a potential antagonist with ileS-binding molecules, recombinant ileS binding molecules, natural substrates or ligands, or substrate or ligand mimetics, under appropriate conditions for a competitive inhibition assay. ileS can be labeled, such as by radioactivity or a colorimetric compound, such that the number of ileS molecules bound to a binding molecule or converted to product can be determined accurately to assess the effectiveness of the potential antagonist.

Potential antagonists include small organic molecules, peptides, polypeptides and antibodies that bind to a polynucleotide or polypeptide of the invention and thereby inhibit or extinguish its activity. Potential antagonists also may be small organic molecules, a peptide, a polypeptide such as a closely related protein or antibody that binds the same sites on a binding molecule, such as a binding molecule, without inducing ileS-induced activities, thereby preventing the action of ileS by excluding ileS from binding.

Potential antagonists include a small molecule that binds to and occupies the binding site of the polypeptide thereby preventing binding to cellular binding molecules, such that normal biological activity is prevented. Examples of small molecules include but are not limited to small organic molecules, peptides or peptide-like molecules. Other potential antagonists include antisense molecules (see Okano, *J. Neurochem.* 56: 560 (1991); *OLIGODEOXYNUCLEOTIDES AS ANTISENSE INHIBITORS OF GENE EXPRESSION*, CRC Press, Boca Raton, Fla. (1988), for a description of these molecules). Preferred potential antagonists include compounds related to and variants of ileS.

Each of the DNA sequences provided herein may be used in the discovery and development of antibacterial compounds. The encoded protein, upon expression, can be used as a target for the screening of antibacterial drugs. Additionally, the DNA sequences encoding the amino terminal regions of the encoded protein or Shine-Delgarno or other translation facilitating sequences of the respective mRNA can be used to construct antisense sequences to control the expression of the coding sequence of interest.

The invention also provides the use of the polypeptide, polynucleotide or inhibitor of the invention to interfere with the initial physical interaction between a pathogen and mammalian host responsible for sequelae of infection. In particular the molecules of the invention may be used: in the prevention of adhesion of bacteria, in particular gram positive bacteria, to mammalian extracellular matrix proteins on in-dwelling devices or to extracellular matrix proteins in wounds; to block ileS protein-mediated mammalian cell invasion by, for example, initiating phosphorylation of mammalian tyrosine kinases (Rosenshine et al., *Infect. Immun.* 60:2211 (1992); to block bacterial adhesion between mammalian extracellular matrix proteins and bacterial ileS proteins that mediate tissue damage and; to block the normal progression of pathogenesis in infections initiated other than by the implantation of in-dwelling devices or by other surgical techniques.

The antagonists and agonists of the invention may be employed, for instance, to inhibit and treat otitis media, conjunctivitis, pneumonia, bacteremia, meningitis, sinusitis, pleural empyema and endocarditis, and most particularly meningitis, such as for example infection of cerebrospinal fluid.

*Helicobacter pylori* (herein *H. pylori*) bacteria infect the stomachs of over one-third of the world's population causing stomach cancer, ulcers, and gastritis (International Agency for Research on Cancer (1994) Schistosomes, Liver Flukes and *Helicobacter Pylori* (International Agency for Research on Cancer, Lyon, France; http://www.uicc.ch/ecp/ecp2904.htm). Moreover, the international Agency for Research on Cancer recently recognized a cause-and-effect relationship between *H. pylori* and gastric adenocarcinoma, classifying the bacterium as a Group I (definite) carcinogen. Preferred antimicrobial compounds of the invention (agonists and antagonists of ileS) found using screens provided by the invention, particularly broad-spectrum antibiotics, should be useful in the treatment of *H. pylori* infection. Such treatment should decrease the advent of *H. pylori*-induced cancers, such as gastrointestinal carcinoma. Such treatment should also cure gastric ulcers and gastritis.

Vaccines

Another aspect of the invention relates to a method for inducing an immunological response in an individual, particularly a mammal which comprises inoculating the individual with ileS, or a fragment or variant thereof, adequate to produce antibody and/or T cell immune response to protect said individual from infection, particularly bacterial infection and most particularly *Streptococcus pneumoniae* infection. Also provided are methods whereby such immunological response slows bacterial replication. Yet another aspect of the invention relates to a method of inducing immunological response in an individual which comprises delivering to such individual a nucleic acid vector to direct expression of ileS, or a fragment or a variant thereof, for expressing ileS, or a fragment or a variant thereof in vivo in order to induce an immunological response, such as, to produce antibody and/or T cell immune response, including, for example, cytokine-producing T cells or cytotoxic T cells, to protect said individual from disease, whether that disease is already established within the individual or not. One way of administering the gene is by accelerating it into the desired cells as a coating on particles or otherwise. Such nucleic acid vector may comprise DNA, RNA, a modified nucleic acid, or a DNA/RNA hybrid.

A further aspect of the invention relates to an immunological composition which, when introduced into an individual capable or having induced within it an immunological response, induces an immunological response in such individual to a ileS or protein coded therefrom, wherein the composition comprises a recombinant ileS or protein coded therefrom comprising DNA which codes for and expresses an antigen of said ileS or protein coded therefrom. The immunological response may be used therapeutically or prophylactically and may take the form of antibody immunity or cellular immunity such as that arising from CTL or CD4+ T cells.

A ileS polypeptide or a fragment thereof may be fused with co-protein which may not by itself produce antibodies, but is capable of stabilizing the first protein and producing a fused protein which will have immunogenic and protective properties. Thus fused recombinant protein, preferably further comprises an antigenic co-protein, such as lipoprotein D from *Hemophilus influenzae*, Glutathione-S-transferase (GST) or beta-galactosidase, relatively large co-proteins which solubilize the protein and facilitate production and purification thereof. Moreover, the co-protein may act as an adjuvant in the sense of providing a generalized stimulation of the immune system. The co-protein may be attached to either the amino or carboxy terminus of the first protein.

Provided by this invention are compositions, particularly vaccine compositions, and methods comprising the polypeptides or polynucleotides of the invention and immunostimulatory DNA sequences, such as those described in Sato, Y. et al. *Science* 273: 352 (1996).

Also, provided by this invention are methods using the described polynucleotide or particular fragments thereof which have been shown to encode non-variable regions of bacterial cell surface proteins in DNA constructs used in such genetic immunization experiments in animal models of infection with *Streptococcus pneumoniae* will be particularly useful for identifying protein epitopes able to provoke a prophylactic or therapeutic immune response. It is believed that this approach will allow for the subsequent preparation of monoclonal antibodies of particular value from the requisite organ of the animal successfully resisting or clearing infection for the development of prophylactic agents or therapeutic treatments of bacterial infection, particularly *Streptococcus pneumoniae* infection, in mammals, particularly humans.

The polypeptide may be used as an antigen for vaccination of a host to produce specific antibodies which protect against invasion of bacteria, for example by blocking adherence of bacteria to damaged tissue. Examples of tissue damage include wounds in skin or connective tissue caused, e.g., by mechanical, chemical or thermal damage or by implantation of indwelling devices, or wounds in the mucous membranes, such as the mouth, mammary glands, urethra or vagina.

The invention also includes a vaccine formulation which comprises an immunogenic recombinant protein of the invention together with a suitable carrier. Since the protein may be broken down in the stomach, it is preferably administered parenterally, including, for example, administration that is subcutaneous, intramuscular, intravenous, or intradermal. Formulations suitable for parenteral administration include aqueous and non-aqueous sterile injection solutions which may contain anti-oxidants, buffers, bacteriostats and solutes which render the formulation isotonic with the bodily fluid, preferably the blood, of the individual; and aqueous and non-aqueous sterile suspensions which may include suspending agents or thickening agents. The formulations may be presented in unit-dose or multi-dose containers, for example, sealed ampules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

While the invention has been described with reference to certain ileS protein, it is to be understood that this covers fragments of the naturally occurring protein and similar proteins with additions, deletions or substitutions which do not substantially affect the immunogenic properties of the recombinant protein.

Compositions, kits and administration

The invention also relates to compositions comprising the polynucleotide or the polypeptides discussed above or their agonists or antagonists. The polypeptides of the invention may be employed in combination with a non-sterile or sterile carrier or carriers for use with cells, tissues or organisms, such as a pharmaceutical carrier suitable for administration to a subject. Such compositions comprise, for instance, a media additive or a therapeutically effective amount of a polypeptide of the invention and a pharmaceutically acceptable carrier or excipient. Such carriers may include, but are not limited to, saline, buffered saline, dextrose, water, glycerol, ethanol and combinations thereof. The formulation should suit the mode of administration. The invention further relates to diagnostic and pharmaceutical packs and kits comprising one or more containers filled with one or more of the ingredients of the aforementioned compositions of the invention.

Polypeptides and other compounds of the invention may be employed alone or in conjunction with other compounds, such as therapeutic compounds.

The pharmaceutical compositions may be administered in any effective, convenient manner including, for instance, administration by topical, oral, anal, vaginal, intravenous, intraperitoneal, intramuscular, subcutaneous, intranasal or intradermal routes among others.

In therapy or as a prophylactic, the active agent may be administered to an individual as an injectable composition, for example as a sterile aqueous dispersion, preferably isotonic.

Alternatively the composition may be formulated for topical application for example in the form of ointments, creams, lotions, eye ointments, eye drops, ear drops, mouthwash, impregnated dressings and sutures and aerosols, and may contain appropriate conventional additives, including, for example, preservatives, solvents to assist drug penetration, and emollients in ointments and creams. Such topical formulations may also contain compatible conventional carriers, for example cream or ointment bases, and ethanol or oleyl alcohol for lotions. Such carriers may constitute from about 1% to about 98% by weight of the formulation; more usually they will constitute up to about 80% by weight of the formulation.

For administration to mammals, and particularly humans, it is expected that the daily dosage level of the active agent will be from 0.01 mg/kg to 10 mg/kg, typically around 1 mg/kg. The physician in any event will determine the actual dosage which will be most suitable for an individual and will vary with the age, weight and response of the particular individual. The above dosages are exemplary of the average case. There can, of course, be individual instances where higher or lower dosage ranges are merited, and such are within the scope of this invention.

In-dwelling devices include surgical implants, prosthetic devices and catheters, i.e., devices that are introduced to the body of an individual and remain in position for an extended time. Such devices include, for example, artificial joints, heart valves, pacemakers, vascular grafts, vascular catheters, cerebrospinal fluid shunts, urinary catheters, continuous ambulatory peritoneal dialysis (CAPD) catheters.

The composition of the invention may be administered by injection to achieve a systemic effect against relevant bacteria shortly before insertion of an in-dwelling device. Treatment may be continued after surgery during the in-body time of the device. In addition, the composition could also be used to broaden perioperative cover for any surgical technique to prevent bacterial wound infections, especially *Streptococcus pneumoniae* wound infections.

Many orthopaedic surgeons consider that humans with prosthetic joints should be considered for antibiotic prophylaxis before dental treatment that could produce a bacteremia. Late deep infection is a serious complication sometimes leading to loss of the prosthetic joint and is accompanied by significant morbidity and mortality. It may therefore be possible to extend the use of the active agent as a replacement for prophylactic antibiotics in this situation.

In addition to the therapy described above, the compositions of this invention may be used generally as a wound treatment agent to prevent adhesion of bacteria to matrix proteins exposed in wound tissue and for prophylactic use in dental treatment as an alternative to, or in conjunction with, antibiotic prophylaxis.

Alternatively, the composition of the invention may be used to bathe an indwelling device immediately before insertion. The active agent will preferably be present at a concentration of 1 µg/ml to 10 mg/ml for bathing of wounds or indwelling devices.

A vaccine composition is conveniently in injectable form. Conventional adjuvants may be employed to enhance the immune response. A suitable unit dose for vaccination is 0.5–5 microgram/kg of antigen, and such dose is preferably administered 1–3 times and with an interval of 1–3 weeks. With the indicated dose range, no adverse toxicological effects will be observed with the compounds of the invention which would preclude their administration to suitable individuals.

Each reference disclosed herein is incorporated by reference herein in its entirety. Any patent application to which this application claims priority is also incorporated by reference herein in its entirety.

EXAMPLES

The examples below are carried out using standard techniques, which are well known and routine to those of skill in the art, except where otherwise described in detail. The examples re illustrative, but do not limit the invention.

Example 1

Strain selection, Library Production and Sequencing

The polynucleotide having the DNA sequence given in SEQ ID NO: 1 was obtained from a library of clones of chromosomal DNA of *Streptococcus pneumoniae* in *E. coli*. The sequencing data from two or more clones containing overlapping *Streptococcus pneumoniae* DNAs was used to construct the contiguous DNA sequence in SEQ ID NO: 1.

Libraries may be prepared by routine methods, for example: Methods 1 and 2 below.

Total cellular DNA is isolated from *Streptococcus pneumoniae* 0100993 according to standard procedures and size-fractionated by either of two methods.

Method 1

Total cellular DNA is mechanically sheared by passage through a needle in order to size-fractionate according to standard procedures. DNA fragments of up to 11 kbp in size are rendered blunt by treatment with exonuclease and DNA polymerase, and EcoRI linkers added. Fragments are ligated into the vector Lambda ZapII that has been cut with EcoRI, the library packaged by standard procedures and *E.coli* infected with the packaged library. The library is amplified by standard procedures.

Method 2

Total cellular DNA is partially hydrolyzed with a one or a combination of restriction enzymes appropriate to generate a series of fragments for cloning into library vectors (e.g., RsaI, PalI, AluI, Bshl235I), and such fragments are size-fractionated according to standard procedures. EcoRI linkers are ligated to the DNA and the fragments then ligated into the vector Lambda ZapII that have been cut with EcoRI, the library packaged by standard procedures, and *E.coli* infected with the packaged library. The library is amplified by standard procedures.

Example 2 ileS Characterization

The enzyme mediated incorporation of radiolabelled amino acid into tRNA may be measured by the aminoacylation method which measures amino acid-tRNA as trichloroacetic acid-precipitable radioactivity from radiolabelled amino acid in the presence of tRNA and ATP (Hughes J, Mellows G and Soughton S, 1980, FEBS Letters, 122:322–324). Thus inhibitors of isoleucyl tRNA synthetase can be detected by a reduction in the trichloroacetic acid precipitable radioactivity relative to the control. Alternatively the tRNA synthetase catalysed partial PPi/ATP exchange reaction which measures the formation of radiolabelled ATP from PPi can be used to detect isoleucyl tRNA synthetase inhibitors (Calender R & Berg P, 1966, *Biochemistry*, 5, 1681–1690).

What is claimed is:

1. An isolated polynucleotide segment comprising a nucleic acid sequence comprising SEQ ID NO:1, wherein the nucleic acid sequence is not genomic DNA.

2. A vector comprising the isolated polynucleotide segment of claim 1.

3. An isolated host cell comprising the vector of claim 2.

4. A process for producing a polypeptide comprising culturing the host cell of claim 3 under conditions sufficient for the production of the polypeptide.

5. An isolated polynucleotide segment comprising a nucleic acid sequence that encodes a polypeptide comprising SEQ ID NO:2, wherein the nucleic acid sequence is not genomic DNA.

6. A vector comprising the isolated polynucleotide segment of claim 5.

7. An isolated host cell comprising the vector of claim 6.

8. A process for producing a polypeptide comprising culturing the host cell of claim 7 under conditions sufficient for the production of the polypeptide.

9. An isolated polynucleotide segment comprising a nucleic acid sequence that encodes a polypeptide consisting of SEQ ID NO:2, wherein the nucleic acid sequence is not genomic DNA.

10. A vector comprising the isolated polynucleotide segment of claim 9.

11. An isolated host cell comprising the vector of claim 10.

12. A process for producing a polypeptide comprising culturing the host cell of claim 11 under conditions sufficient for the production of the polypeptide.

* * * * *